United States Patent
Saunthararajah et al.

(10) Patent No.: US 9,926,316 B2
(45) Date of Patent: Mar. 27, 2018

(54) ANTITUMOR DERIVATIVES FOR DIFFERENTIATION THERAPY

(71) Applicant: THE CLEVELAND CLINIC FOUNDATION, Cleveland, OH (US)

(72) Inventors: Yogenthiran Saunthararajah, Cleveland Heights, OH (US); Kwok Peng Ng, Avon, OH (US); James G. Phillips, Bay Village, OH (US); Babal Kant Jha, Shaker Heights, OH (US); Anand Dev Tiwari, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 15/449,013

(22) Filed: Mar. 3, 2017

(65) Prior Publication Data

US 2017/0253589 A1 Sep. 7, 2017

Related U.S. Application Data

(60) Provisional application No. 62/303,062, filed on Mar. 3, 2016.

(51) Int. Cl.
| | |
|---|---|
| C07D 401/02 | (2006.01) |
| A61K 31/437 | (2006.01) |
| A61K 31/4353 | (2006.01) |
| C07D 401/10 | (2006.01) |
| C07D 471/04 | (2006.01) |

(52) U.S. Cl.
CPC ................ *C07D 471/04* (2013.01)

(58) Field of Classification Search
CPC .. C07D 401/02; C07D 401/10; A61K 31/437; A61K 31/4353
USPC .......................................... 546/121; 514/300
See application file for complete search history.

(56) References Cited

U.S. PATENT DOCUMENTS

| | | | | |
|---|---|---|---|---|
| 5,204,352 A | * | 4/1993 | Sundberg ............ | C07D 213/53 514/259.1 |
| 6,335,327 B1 | * | 1/2002 | Ogawa ................ | C07D 215/12 514/213.01 |
| 7,566,725 B2 | * | 7/2009 | Fang .................... | C07D 471/04 514/300 |
| 7,714,319 B2 | * | 5/2010 | Nakamura ............ | H01L 51/004 257/40 |
| 8,022,207 B2 | * | 9/2011 | Tanifuji .............. | A61K 51/0455 544/179 |
| 8,277,777 B2 | * | 10/2012 | Tanifuji ............... | C07D 471/04 424/1.11 |
| 8,703,096 B2 | * | 4/2014 | Cai ..................... | A61K 51/0453 424/1.11 |

FOREIGN PATENT DOCUMENTS

| | | | |
|---|---|---|---|
| WO | 2002066477 | * | 8/2002 |
| WO | 2002066478 | * | 8/2002 |

OTHER PUBLICATIONS

Zhuang et al., Journal of Medicinal Chemistry (2003), 46(2), 237-243.*
Cai et al., Journal of Medicinal Chemistry (2007), 50(19), 4746-4758.*
Cai et al., Journal of Medicinal Chemistry (2008), 51(1), 148-158.*
Cosimelli et al., European Journal of Medicinal Chemistry (2014), 83, 45-56.*
Leopoldo et al., Journal of Medicinal Chemistry (2007), 50(20), 5043-5047.*
Chakrabarti, Amitabha, et al. "ATP depletion triggers acute myeloid leukemia differentiation through an ATR/Chk1 protein-dependent and p53 protein-independent pathway." *Journal of Biological Chemistry* 287.28 (2012): 23635-23643.
Ferrara, Fabiana F., et al. "Histone deacetylase-targeted treatment restores retinoic acid signaling and differentiation in acute myeloid leukemia." *Cancer research* 61.1 (2001): 2-7.
Fiskus, Warren et al. "Highly Effective Combination of LSD1 (KDM1A) Antagonist and Pan-Histone Deacetylase Inhibitor against Human AML Cells." *Leukemia* 28.11 (2014): 2155-2164. PMC. Web. Aug. 10, 2017.
Gu, Xiaorong, et al. "Runx1 regulation of Pu. 1 corepressor/coactivator exchange identifies specific molecular targets for leukemia differentiation therapy." *Journal of Biological Chemistry* 289.21 (2014): 14881-14895.

(Continued)

*Primary Examiner* — Niloofar Rahmani
(74) *Attorney, Agent, or Firm* — Tarolli, Sundheim, Covell & Tummino LLP

(57) ABSTRACT

Imidazopyridine derivatives according to formula I are described

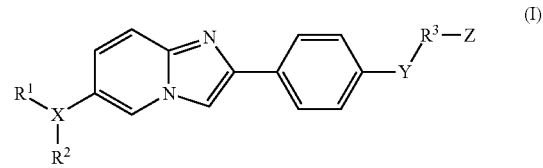

wherein X is selected from CH, N, S, and O, Y is selected from S, CO, and O, $R^1$ and optional $R^2$ are independently selected from H, OH, substituted or unsubstituted $C_1$-$C_6$ alkyl, and substituted or unsubstituted $C_4$-$C_6$ cycloalkyl or cycloheteroalkyl, $R^3$ is selected from H, OH, substituted or unsubstituted $C_1$-$C_6$ alkyl, and optional Z is selected from OH, $NH_2$, $NH(CO)R^4$, $NH(SO_2)R^4$, guanidine, alkylguanidine, and fluoroguanidine, $R^4$ is polyethylene glycol or substituted or unsubstituted $C_1$-$C_6$ alkyl, and pharmaceutically acceptable salt thereof. The imidazopyridine derivatives can be used for treatment of cancer in a subject.

20 Claims, 18 Drawing Sheets

(56) References Cited

OTHER PUBLICATIONS

Gupta K, Chakrabarti A, Rana S, Ramdeo R, Roth BL, et al. (2011) Securinine, a Myeloid Differentiation Agent with Therapeutic Potential for AML. PLOS ONE 6(6): e21203. https://doi.org/10.1371/journal.pone.0021203.
Hu, Zhenbo, and Yogen Saunthararajah. "CEBPE activation in PML-RARA cells by arsenic." *Blood* 119.9 (2012): 2177-2179. Web. Aug. 10, 2017.
Ignatz-Hoover, James J et al. "The Role of TLR8 Signaling in Acute Myeloid Leukemia Differentiation." *Leukemia* 29.4 (2015): 918-926. *PMC*. Web. Aug. 10, 2017.
Iida et al. "Protein Expression and Constitutive Phosphorylation of Jematopoietic Transcription Factors PU.1 and C/EBPβ in Acute Myeloid Leukemia Blasts." *Int J Hematol*, 72(2):153-8 (2000).
Jan, Max et al. "Clonal Evolution of Pre-Leukemic Hematopoietic Stem Cells Precedes Human Acute Myeloid Leukemia." *Science translational medicine* 4.149 (2012): 149ra118. *PMC*. Web. Aug. 10, 2017.
Kinzler, Kenneth W., and Bert Vogelstein. "Cancer therapy meets p53." *New England Journal of Medicine* 331.1 (1994): 49-50.
Lipinski, Christopher A. "Lead-and drug-like compounds: the rule-of-five revolution." *Drug Discovery Today: Technologies* 1.4 (2004): 337-341.
Mandelli, Franco, et al. "A randomised clinical trial comparing idarubicin and cytarabine to daunorubicin and cytarabine in the treatment of acute non-lymphoid leukaemia." *European Journal of Cancer and Clinical Oncology* 27.6 (1991): 750-755.
Matsushita, H., et al. "C/EBP [alpha] and C/EBP [varepsilon] induce the monocytic differentiation of myelomonocytic cells with the MLL-chimeric fusion gene." *Oncogene* 27.53 (2008): 6749.
Negrotto, Soledad et al. "CpG Methylation Patterns and Decitabine Treatment Response in Acute Myeloid Leukemia Cells and Normal Hematopoietic Precursors." *Leukemia* 26.2 (2012): 244-254. *PMC*. Web. Aug. 10, 2017.
Radomska, Hanna S. et al. "Targeting CDK1 Promotes FLT3-Activated Acute Myeloid Leukemia Differentiation through C/EBPα." *The Journal of Clinical Investigation* 122.8 (2012): 2955-2966. *PMC*. Web. Aug. 10, 2017.
Radomska, Hanna S., et al. "A cell-based high-throughput screening for inducers of myeloid differentiation." *Journal of biomolecular screening* 20.9 (2015): 1150-1159.
Roberts, Daniel A., et al. "Low efficacy and high mortality associated with clofarabine treatment of relapsed/refractory acute myeloid leukemia and myelodysplastic syndromes." *Leukemia research* 39.2 (2015): 204-210.
Saunthararajah Y, Sekeres M, Advani A, et al. Evaluation of noncytotoxic DNMT1-depleting therapy in patients with myelodysplastic syndromes. *The Journal of Clinical Investigation*. 2015;125(3):1043-1055. doi:10.1172/JCI78789.
Saunthararajah, Yogen et al. "P53-Independent, Normal Stem Cell Sparing Epigenetic-Differentiation Therapy for Myeloid and Other Malignancies." *Seminars in oncology* 39.1 (2012): 97-108. *PMC*. Web. Aug. 10, 2017.
Saunthararajah, Yogen. "Targets of opportunity for precision medicine." *Blood* 125.20 (2015): 3041-3042. Web. Aug. 10, 2017.
Smith, Matthew L., Robert K. Hills, and David Grimwade. "Independent prognostic variables in acute myeloid leukaemia." *Blood reviews* 25.1 (2011): 39-51.
Toledo, Franck, and Geoffrey M. Wahl. "Regulating the p53 pathway: in vitro hypotheses, in vivo veritas." Nature Reviews| Cancer 6 (2006): 909.
Wald, David N., et al. "Identification of 6-benzylthioinosine as a myeloid leukemia differentiation-inducing compound." *Cancer research* 68.11 (2008): 4369-4376.
Wang, Fang, et al. "Targeted inhibition of mutant IDH2 in leukemia cells induces cellular differentiation." *Science* 340.6132 (2013): 622-626.
Wong, Terrence N. et al. "The Role of TP53 Mutations in the Origin and Evolution of Therapy-Related AML." *Nature* 518.7540 (2015): 552-555. *PMC*. Web. Aug. 10, 2017.
Wunderlich, Mark et al "AML cells are differentially sensitive to chemotherapy treatment in a human xenograft model." Blood 121.12 (2013): e90-e97. Web. Aug. 18, 2017.
Yin, Bin, et al. "Trp53 loss during in vitro selection contributes to acquired Ara-C resistance in acute myeloid leukemia." *Experimental hematology* 34.5 (2006): 631-641.

\* cited by examiner

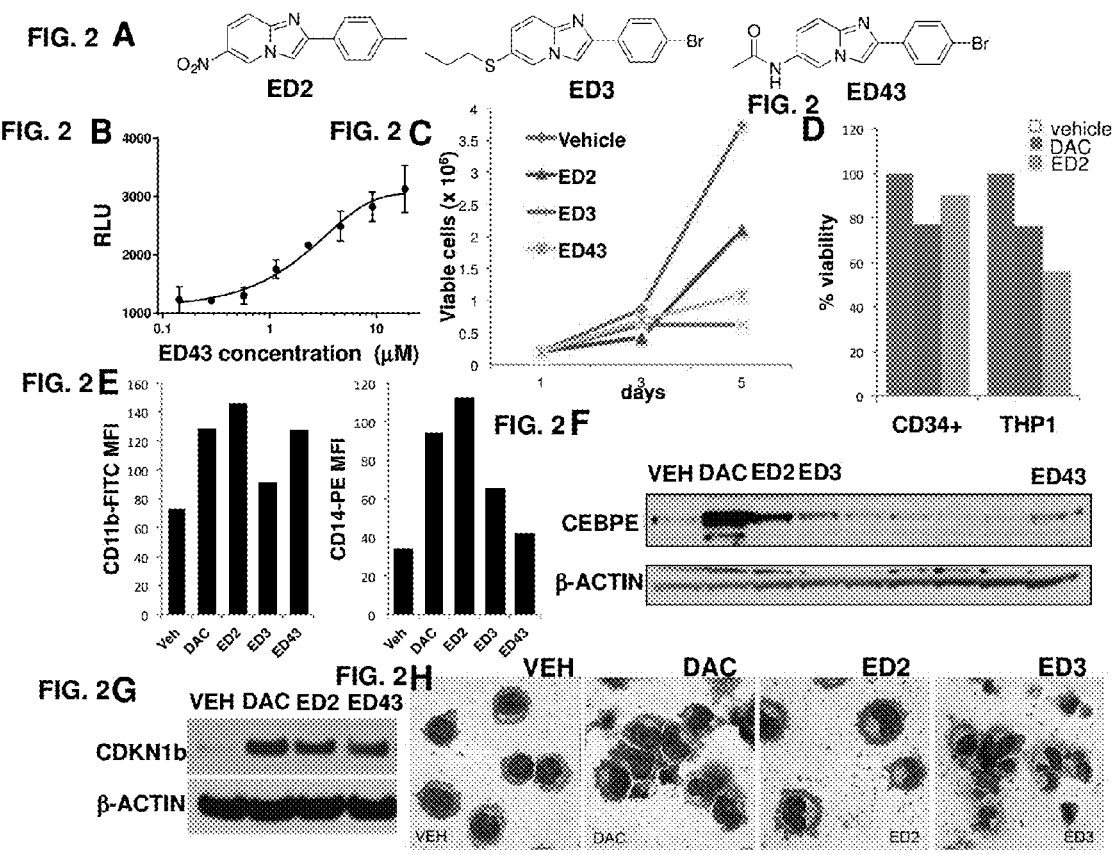

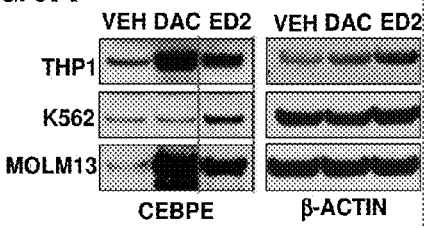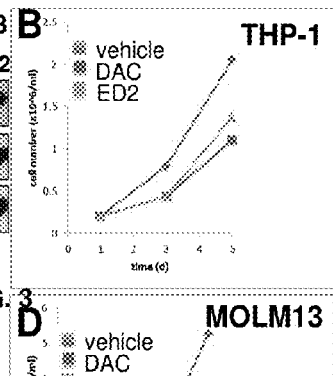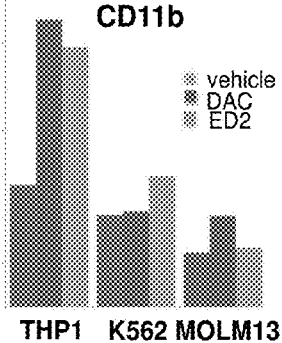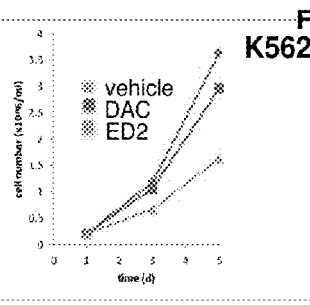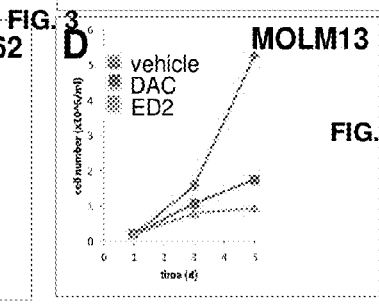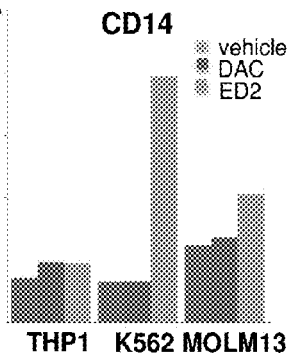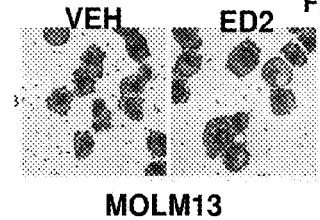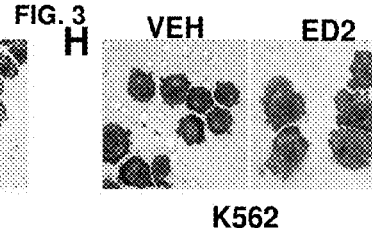

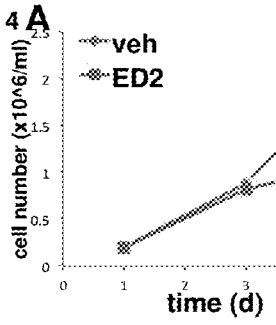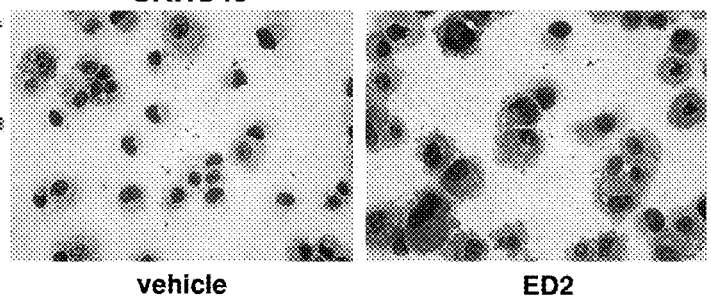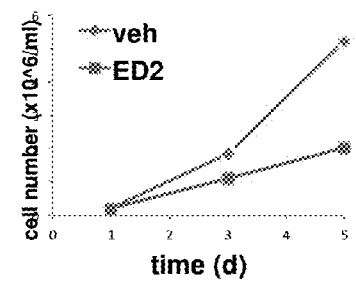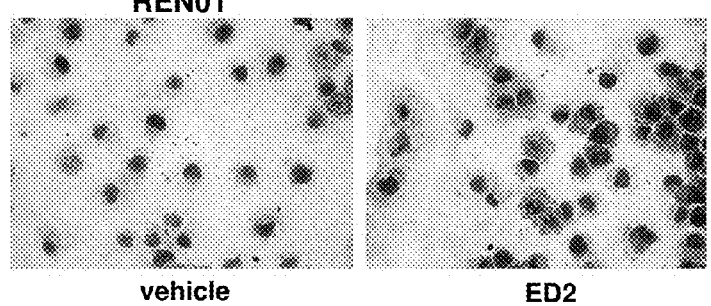

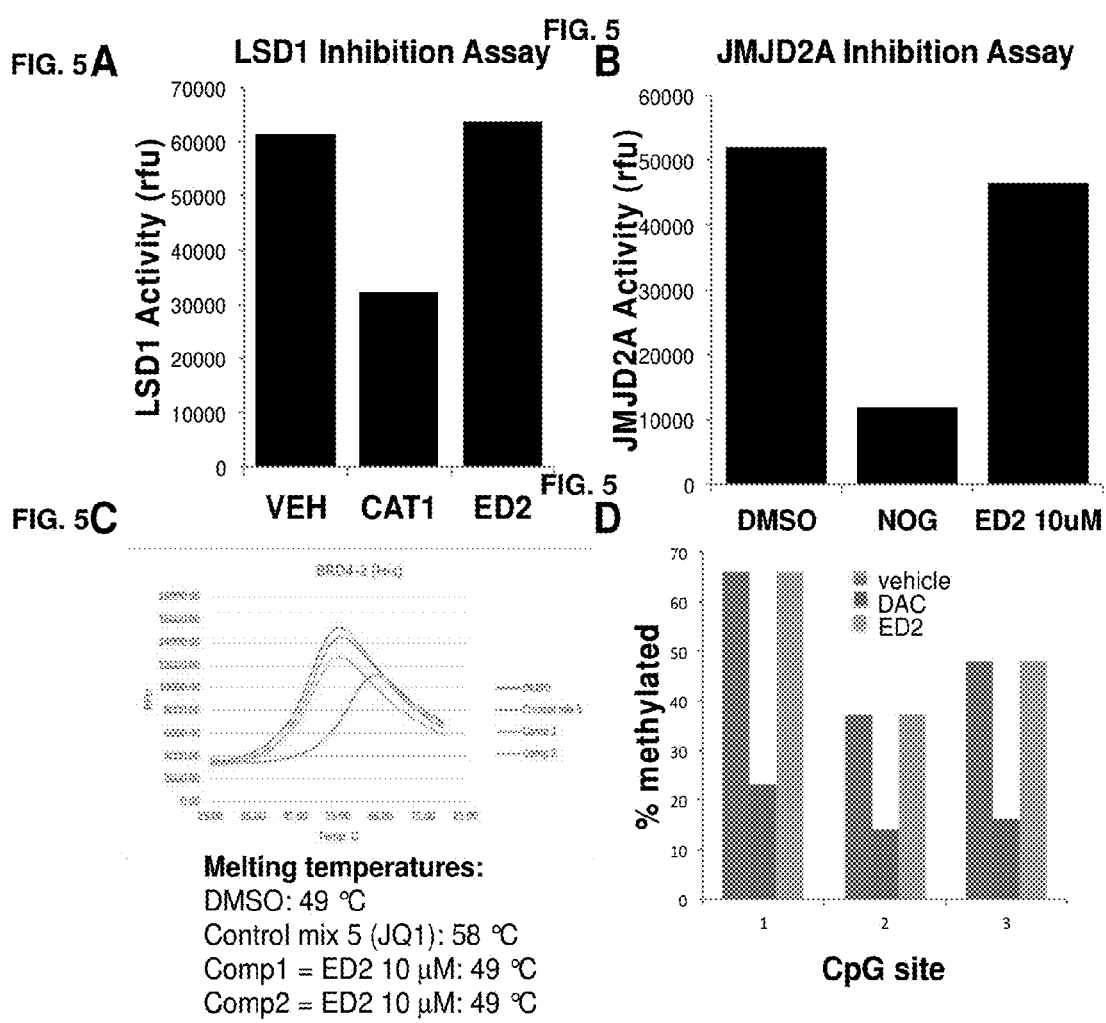

ANTITUMOR DERIVATIVES FOR DIFFERENTIATION THERAPY

CONTINUING APPLICATION DATA

This application claims the benefit of U.S. Provisional Application Ser. No. 62/303,062, filed Mar. 3, 2016, the disclosure of which is incorporated by reference herein.

BACKGROUND

Most acute myeloid leukemia (AML) is lethal due to relapse that is typically resistant to 2nd or 3rd-line treatments. How et al., Blood Cancer J., 3:e116 (2013). Why do 1st-line treatments select for AML cells somehow resistant to subsequent treatments targeting different molecules? One reason is that treatments overlap in final pathways of action despite distinct proximal molecular targets: current treatments induce apoptosis (cytotoxicity), via stress applied upstream of p53, the master transcription factor (TF) regulator of apoptosis. In some AML cases, p53-system attenuation by genetic alterations to TP53, MDM2/4 etc. subverts this common apoptotic intent, causing resistance in vitro and clinically, as demonstrated. Wong et al., Nature, 518(7540): 552-5 (2015). The same treatments destroy normal hematopoietic stem cells (HSC) with intact p53, causing substantial toxicities including death. Brennig et al., Cytotherapy, 14(4):451-60 (2012).

What is needed therefore is not just new treatments, but treatments that use pathways other than p53/apoptosis for cell cycle exits. Differentiation, not apoptosis, is the p53-independent pathway normally terminating myeloid precursor proliferation (billions of cells daily), and myeloid differentiation failure defines and diagnoses AML and a variety of other types of cancer. Two drugs, retinoic acid (ATRA) and arsenic trioxide, are FDA-approved for non-cytotoxic differentiation-restoring treatment of a rare sub-type of AML, acute promyelocytic leukemia (APL), and have transformed APL from worst to best in AML outcomes. Smith et al., Blood Reviews, 25(1):39-51 (2011); Hu Z, Saunthararajah Y., Blood, 119(9):2177-9 (2012). However, while ATRA and arsenic are strikingly curative, they are only effective for treating the very rare AML sub-type APL, since both agents specifically interact with the fusion protein PML-RARA that is unique to this leukemia.

Although conventional cytotoxic treatments for AML can have differing proximal actions, e.g., topoisomerase inhibition (daunorubicin) or termination of DNA chain synthesis (cytarabine), a final common pathway converges onto p53 (TP53), a master regulator of apoptosis (cytotoxicity). Kinzler K W, Vogelstein B., N Engl J Med., 331(1):49-50 (1994). As such, TP53 mutation/deletion is associated with resistance to treatments in vitro (Yin et al., Exp Hematol., 34(5):631-41 (2006)) and in vivo. TP53-mutated AML treated with daunorubicin and/or cytarabine had a response rate of 33% compared to 81% for TP53 wild-type AML (Wattel et al., Blood, 84(9):3148-57 (1994)), and chemotherapy has been shown to select for TP53 mutated AML sub-clones at relapse. Wong et al., Nature, 518(7540):552-5 (2015). Even if TP53 itself is not mutated, alterations in other key p53-system genes are frequent, e.g., gains in MDM4, which inactivates p53, are very common in highly chemorefractory sub-types of AML. Toledo F, Wahl G M, Nat Rev Cancer, 6(12):909-23 (2006). Meanwhile, cytotoxic treatments damage residual normal hematopoietic stem cells (HSC) and stroma, causing significant toxicities including fatal exacerbations of low blood counts in as many as 29% of patients treated. Roberts et al., Leukemia research, 39(2): 204-10 (2015). Damage to normal stem cells is especially a problem in treating myeloid malignancies, where residual normal HSC are needed to reverse the low blood counts that are the cause of morbidity and death. Mandelli et al., European journal of cancer, 27(6):750-5 (1991). To spare normal HSC, treatments should exploit a difference between normal HSC and AML-initiating cells (leukemia stem cells).

SUMMARY OF THE INVENTION

The inventors have identified a difference that can spare healthy cells such as HSC while still inhibiting cancer cells. AML-initiating cells express very high levels of master differentiation-driving transcription factor (TF) (e.g., CEBPA, PU.1), not master stem cell TF (e.g., HLF, PRDM5) (FIG. 1A). Iida et al., Int J Hematol., 71(2):153-8 (2000). In other words, AML-initiating cells differ from normal HSC in being poised for differentiation in terms of their master TF context. In fact, key 2nd or 3rd hits in the multi-hit process of leukemogenesis have been shown by several groups to occur in committed progenitors, not in HSC (Jan et al., Sci Transl Med., 4(149):149ra18 (2012)); the founder genetic mutation, e.g., in DNMT3A, occurs in HSC. The inventors have previously shown that this master TF difference could be exploited for remarkably safe and effective noncytotoxic therapy to treat high risk myeloid malignancies, including TP53-null cases (Saunthararajah et al., J Clin Invest., 125 (3):1043-55 (2015)), and it is intriguing to note that APL, the AML sub-type with the best long-term survival outcomes, is the only AML sub-type in which differentiation therapy (with ATRA and arsenic) is the standard 1st-line treatment. Smith et al., Blood Reviews, 25(1):39-51 (2011). Also noteworthy is that experimental and clinical evidence demonstrates that APL is not unique amongst AMLs in being poised for differentiation. Rather, rational differentiation treatments based on mechanisms of disease have not been adequately devised and evaluated, but can be remarkably safe and effective when so-devised and applied. Saunthararajah et al., Semin Oncol., 39(1):97-108 (2012).

Differentiation-mediated cell cycle exits of AML cells, like those that occur during normal tissue differentiation, do not require the p53-system, and are readily induced in p53/p16-null, chemo-resistant AML cells. Saunthararajah Y., Blood, 125(20):3041-2 (2015). The dearth of p53-independent, normal stem cell sparing differentiation-restoring oncotherapeutics in the clinic likely reflects the lack of understanding of the molecular mechanisms that effect differentiation arrest in AML, as well as a continued view that induction of apoptosis of cancer cells is a desirable property (ignoring underlying therapeutic-index issues from p53-mediated toxic damage to normal stem cells). Additionally, differentiation-inducing molecules may only show effects beyond the time horizon of typical cell viability assays, requiring distinct assay strategies.

Chemical probes modulating differentiation in AML are known. These compounds include the following: decitabine, for which clinical induction of differentiation at sub-cytotoxic doses (DNMT1 depletion) has been demonstrated; histone deacetylase inhibitors (known inducers of DNA damage) (Ferrara et al., Cancer research, 61(1):2-7 (2001)); 6-benzyl-thioinosine (Wald et al., Cancer research, 68(11): 4369-76 (2008)) (ATP depletion/DNA damage (Chakrabarti et al., J.B.C., 287(28):23635-43 (2012))); securinine (DNA damage (Gupta et al., PloS one, 6(6):e21203 (2011))); CDK1 inhibitors in FLT3 mutant AML (Radomska et al., J Clin Invest., 122(8):2955-66 (2012)); R848 (TLR8 agonist)

(Ignatz-Hoover et al., Leukemia, 29(4):918-26 (2015)); SP2509 (histone demethylase LSD1 inhibitor) (Fiskus et al., Leukemia, 28(11):2155-64 (2014)); IDH2 inhibitors, in the low percentage of cases where change-of-function IDH2 mutations are found (Wang et al., Science, 340(6132):622-6 (2013)); and ICCB280 (unknown mechanism) (Radomska et al., J. Biomol Screen, 20(9):1150-9 (2015)). These studies confirm that multiple pathways can induce terminal differentiation and testify to the clinical interest that surrounds novel inducers of cancer cell differentiation. The inventors have investigated mechanisms that induce differentiation broadly across a variety of different AML subtypes without inducing DNA damage, which has the potential to cause off-target toxicity and DNA alterations that can be cancer-causing. The chemical structures of the lead series of compounds is dissimilar to known compounds, and the data obtained shows that the newly identified compounds have striking differentiation-inducing effects in some solid tumor-derived cell lines as well.

BRIEF DESCRIPTION OF THE FIGURES

FIG. 2A-FIG. 2H provide graphs and images showing ED2 and close analogs induce phenotypes associated with differentiation. All experiments are with THP1 AML cells treated for 4 d with 200 nM decitabine (DAC) or 10 µM ED2/3/43, except D&F, 2d treatment, readout day 4. A) ED2/3/43. B) Dose-response of ED43 in CEBPE luciferase reporter assay. C) ED2/3/43 induce gradual reductions of cell number. D) ED2 does not affect viability in CD34+ normal HSCs. E) Elevation of differentiation markers CD11b and CD14. F) Upregulation of CEBPE protein. G) Upregulation of p27 (CDKN1B) (ED3 lysates were unavailable). H) Giemsa staining demonstrating secondary granule formation and morphology changes indicative of granulocytic differentiation.

FIGS. 3A-3H provide graphs and images showing ED2 induces differentiation of multiple AML cell lines. All experiments are with cells treated for 2 d with 200 nM decitabine (DAC) or 10 µM ED2, then measured 4d after plating. A) Upregulation of CEBPE by ED2 highlighted with red box. B-D) Effects of ED2 on cell number. E-F) Elevation of differentiation markers CD11b and CD14. G-H) Giemsa staining shows altered size and morphology.

FIGS. 4A-4D provide graphs and images showing ED2 induces differentiation of renal cell carcinoma cell lines. All experiments are with cells treated for 4 d with 10 µM ED2. A-B) Effects on viability in SKRC45 and REN01 cells. C-D) Giemsa staining demonstrating altered cell size and morphology.

FIG. 5A-FIG. 5D provide graphs showing ED2 does not induce differentiation by several known mechanisms. A-B) Biochemical assay for the histone demethylases LSD1 and JMJD2A, positive control was the catecholamine analogue CAT1 for LSD1 and NOG for JMJD2A. C) Melting temperatures for the $2^{nd}$ bromodomain of BRD4 show no interaction with ED2 (Comp1 and Comp2, duplicate measurements). Equivalent results were obtained for the $1^{st}$ bromodomain of BRD4. D) Percentage of methylation obtained by pyrosequencing of three proximal CpG sites in the LINE1 retrotransposon. Positive control for DNMT1-inhibition was decitabine (DAC).

DETAILED DESCRIPTION OF THE INVENTION

Figure 1:
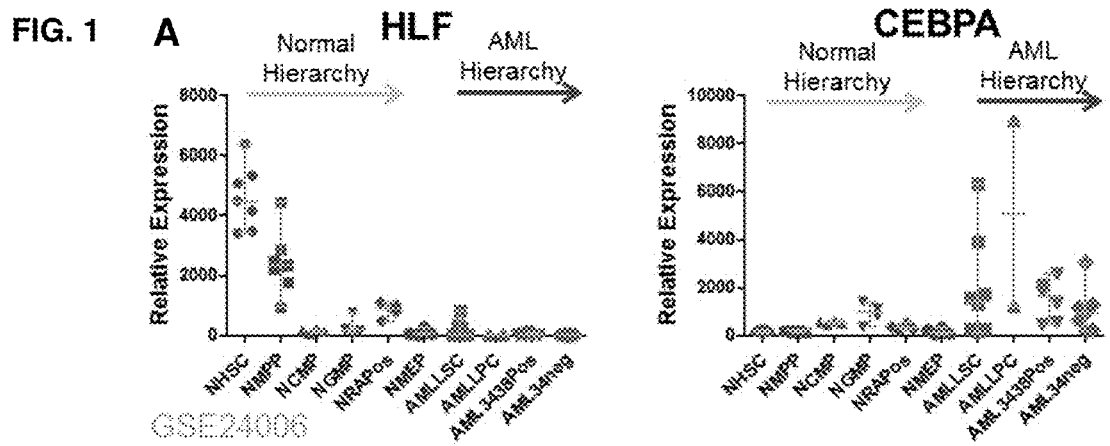
FIG. 1A and FIG. 1B provide graphs and schemes showing aberrant transcription factor expression and activity distinguishes AML cells from normal HSCs. A) Expression of master TF that make HSC (HLF) and granulocytes (CEBPA), in normal hematopoietic hierarchy and AML hierarchy (NHSC=normal HSC, AML LSC=Leukemia stem cells). B) Design of a high-throughput screen to identify noncytotoxic molecules inducing differentiation by upregulation of CEBPE.
Figure 1:
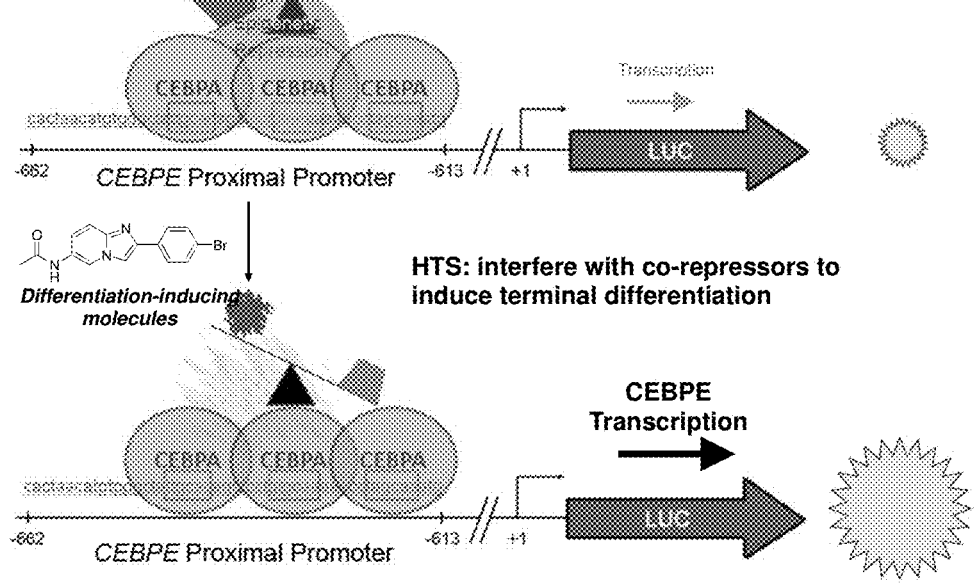

The present invention provides imidazopyridine derivatives according to formula I:

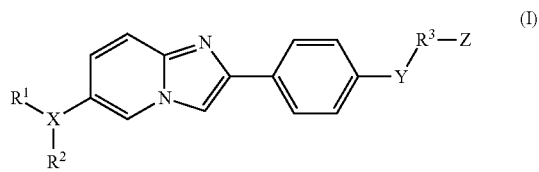

wherein X is selected from CH, N, S, and O, Y is selected from S, CO, NH, NO, and O, $R^1$ and optional $R^2$ are independently selected from H, OH, substituted or unsubstituted $C_1$-$C_6$ alkyl, substituted or unsubstituted $C_4$-$C_6$ cycloalkyl or cycloheteroalkyl, and aryl; $R^3$ is selected from H, OH, substituted or unsubstituted $C_1$-$C_6$ alkyl, and optional Z is selected from OH, $NH_2$, NH(CO)$R^4$, NH(SO$_2$)$R^4$, guanidine, alkylguanidine, and fluoroguanidine, $R^4$ is polyethylene glycol or substituted or unsubstituted $C_1$-$C_6$ alkyl, and pharmaceutically acceptable salt thereof. The imidazopyridine derivatives can be used for treatment of cancer in a subject.

Definitions

The terminology as set forth herein is for description of the embodiments only and should not be construed as limiting of the invention as a whole. Unless otherwise specified, "a," "an," "the," and "at least one" are used interchangeably. Furthermore, as used in the description of the invention and the appended claims, the singular forms "a", "an", and "the" are inclusive of their plural forms, unless contraindicated by the context surrounding such.

The terms "comprising" and variations thereof do not have a limiting meaning where these terms appear in the description and claims.

As used herein, the term "organic group" is used for the purpose of this invention to mean a hydrocarbon group that is classified as an aliphatic group, cyclic group, or combination of aliphatic and cyclic groups (e.g., alkaryl and aralkyl groups). In the context of the present invention, suitable organic groups for imidazopyridine derivatives are those that do not interfere with the compounds anticancer activity. In the context of the present invention, the term "aliphatic group" means a saturated or unsaturated linear or branched hydrocarbon group. This term is used to encompass alkyl, alkenyl, and alkynyl groups, for example.

As used herein, the terms "alkyl", "alkenyl", and the prefix "alk-" are inclusive of straight chain groups and branched chain groups and cyclic groups, e.g., cycloalkyl and cycloalkenyl. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Lower alkyl groups are those including at most 6 carbon atoms. Examples of alkyl groups include haloalkyl groups and hydroxyalkyl groups.

Unless otherwise specified, "alkylene" and "alkenylene" are the divalent forms of the "alkyl" and "alkenyl" groups defined above. The terms, "alkylenyl" and "alkenylenyl" are used when "alkylene" and "alkenylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like. A halo moiety can be chlorine, bromine, fluorine, or iodine.

Cycloalkyl groups are cyclic alkyl groups containing 3, 4, 5, 6, 7 or 8 ring carbon atoms like cyclopropyl, cyclobutyl, cyclopentyl, cyclohexyl or cyclooctyl, which can also be substituted and/or contain 1 or 2 double bounds (unsaturated cycloalkyl groups) like, for example, cyclopentenyl or cyclohexenyl can be bonded via any carbon atom.

A heterocyclyl group means a mono- or bicyclic ring system in which one or more carbon atoms can be replaced by one or more heteroatoms such as, for example, 1, 2 or 3 nitrogen atoms, 1 or 2 oxygen atoms, 1 or 2 sulfur atoms or combinations of different hetero atoms. The heterocyclyl residues can be bound at any positions, for example on the 1-position, 2-position, 3-position, 4-position, 5-position, 6-position, 7-position or 8-position.

The term "aryl" as used herein includes carbocyclic aromatic rings or ring systems. Examples of aryl groups include phenyl, naphthyl, biphenyl, anthracenyl, phenanthracenyl, fluorenyl and indenyl. Aryl groups may be substituted or unsubstituted.

Unless otherwise indicated, the term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

When a group is present more than once in any formula or scheme described herein, each group (or substituent) is independently selected, whether explicitly stated or not. For example, for the formula —C(O)—NR$_2$ each R group is independently selected. In addition, in some embodiments, a group is identified as being optional. An optional group may be entirely absent in some embodiments of the invention, but present in others.

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, tert-butyl, and the like.

"Treat", "treating", and "treatment", etc., as used herein, refer to any action providing a benefit to a patient at risk for or afflicted with a disease, including improvement in the condition through lessening or suppression of at least one symptom, delay in progression of the disease, prevention or delay in the onset of the disease, etc. Treatment also includes partial or total destruction or differentiation of the undesirable proliferating cells with minimal effects on normal cells. In accordance with the present invention, desired mechanisms of treatment at the cellular level include stimulation of differentiation in cancer and pre-cancer cells.

As used herein, the term "prevention" includes either preventing the onset of a clinically evident unwanted cell proliferation altogether or preventing the onset of a preclinically evident stage of unwanted rapid cell proliferation in individuals at risk. Also intended to be encompassed by this definition is the prevention of metastasis of malignant cells or to arrest or reverse the progression of malignant cells. This includes prophylactic treatment of those having an enhanced risk of developing precancers and cancers. An elevated risk represents an above-average risk that a subject will develop cancer, which can be determined, for example, through family history or the detection of genes causing a predisposition to developing cancer.

"Pharmaceutically acceptable" as used herein means that the compound or composition is suitable for administration to a subject to achieve the treatments described herein, without unduly deleterious side effects in light of the severity of the disease and necessity of the treatment.

The terms "therapeutically effective" and "pharmacologically effective" are intended to qualify the amount of each agent which will achieve the goal of decreasing disease severity while avoiding adverse side effects such as those typically associated with alternative therapies. The therapeutically effective amount may be administered in one or more doses. An effective amount, on the other hand, is an amount sufficient to provide a significant chemical effect, such as the inhibition of cancer growth by a detectable amount.

A "subject," as used herein, can be any animal, and may also be referred to as the patient. Preferably the subject is a vertebrate animal, and more preferably the subject is a mammal, such as a domesticated farm animal (e.g., cow, horse, pig) or pet (e.g., dog, cat). In some embodiments, the subject is a human.

Imidazopyridine Derivatives

In one aspect, the present invention provides differentiation-inducing compounds. The differentiation inducing compounds include imidazopyridine derivatives, which are compounds based on the imidazo[1,2-a]pyridine heterocycle chemical structure. The inventors have determined that active compounds can include a variety of substituents at the C6 and C4' positions on the imidazo[1,2-a]pyridine backbone. For example, see FIG. 8 which shows a wide variety of different imidazopyridine derivatives. Imidazopyridine derivatives, as defined herein, include the compounds of formula I:

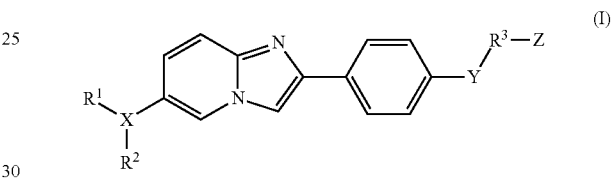

wherein X is selected from CH, N, S, and O, Y is selected from S, CO, NH, NO, and O, $R^1$ and optional $R^2$ are independently selected from H, OH, substituted or unsubstituted $C_1$-$C_6$ alkyl, substituted or unsubstituted $C_4$-$C_6$ cycloalkyl or cycloheteroalkyl, and aryl; $R^3$ is selected from H, OH, substituted or unsubstituted $C_1$-$C_6$ alkyl, and optional Z is selected from OH, $NH_2$, $NH(CO)R^4$, $NH(SO_2)R^4$, guanidine, alkylguanidine, and fluoroguanidine, $R^4$ is polyethylene glycol or substituted or unsubstituted $C_1$-$C_6$ alkyl, and pharmaceutically acceptable salt thereof.

The inventors have determined that a variety of substituents can be used at the C6 position along the imidazo[1,2-a]pyridine backbone. Structure-activity studies and molecular modeling studies have shown that a variety of hydrophobic groups at the C6 position can be used that increase the binding specificity of the compound for SMARCA5, which the inventors have identified as a likely target for compounds of the invention. Accordingly, X can be selected from CH, N, S, and O, and $R^1$ and optional $R^2$ are independently selected from H, OH, substituted or unsubstituted $C_1$-$C_6$ alkyl, substituted or unsubstituted $C_4$-$C_6$ cycloalkyl or cycloheteroalkyl, and aryl. In some embodiments, X is S, $R^1$ unsubstituted $C_1$-$C_6$ alkyl, and $R^2$ is absent, while in further embodiments X is S and $R^1$ is butyl (e.g., n-butyl). In additional embodiments, X is CH, $R^1$ is $C_1$-$C_6$ alkyl, and $R^2$ is H or $C_1$-$C_6$ alkyl so that the C6 position includes an alkyl group. In further embodiments, X is N, $R^1$ is $C_1$-$C_6$ alkyl, and $R^2$ is $C_1$-$C_6$ alkyl.

The inventors have also determined that a variety of substituents can be used at the C4' position along the imidazo[1,2-a]pyridine backbone, which is the para position of the phenyl ring. Structure-activity studies and molecular modeling studies have shown that a variety of polar groups at the C4' position can be used that increase the binding specificity of the compound for SMARCA5, which the inventors have identified as a likely target for compounds of the invention, as well as increasing the solubility of the compound. Preferably the group at C4' is capable of forming a salt bridge or hydrogen bond to the SMARCA5 molecule. Accordingly, Y can be selected from S, CO, NH, NO, and O, $R^3$ can be selected from H, OH, substituted or unsubstituted $C_1$-$C_6$ alkyl, and optional Z is selected from OH, $NH_2$, $NH(CO)R^4$, $NH(SO_2)R^4$, guanidine, alkylguanidine, and fluoroguanidine, and $R^4$ is polyethylene glycol or substituted or unsubstituted $C_1$-$C_6$ alkyl. In some embodiments, Y is O, $R^3$ is $C_1$-$C_6$ alkyl, and Z is $NH_2$. In other embodiments, the combined groups Y—R—Z are $CO_2H$, OH, or CHO, so that the C4' is substituted with a polar carboxyl, hydroxyl, or aldehyde group. In other embodiments, the Z group can include a further alkyl group. For example, in some embodiments, Y is O, $R^3$ is $C_1$-$C_6$ alkyl, and Z is $NH(CO)R^4$, $NH(SO_2)R^4$, wherein $R^4$ is polyethylene glycol or substituted or unsubstituted $C_1$-$C_6$ alkyl.

The inventors have carried out a number of tests demonstrating the activity of two compounds in particular. Accordingly, in some embodiments, the differentiation-inducing compound is

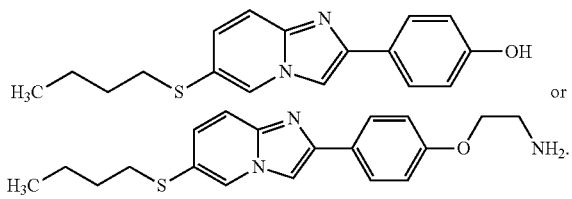

or

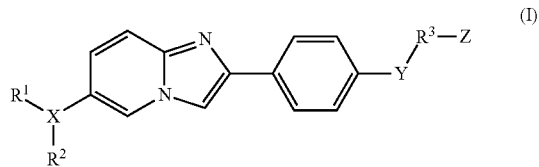

Treatment of Cancer Using Imidazopyridine Derivatives

In another aspect, the present invention provides methods for treating or preventing cancer in a subject using an imidazopyridine derivative. A method of treating or preventing cancer in a subject in need thereof includes administering a therapeutically effective amount of pharmaceutically acceptable formulation comprising a compound of Formula I:

(I)

Formula 1 provides a core imidazo[1,2-a]pyridine structure with variable substituents at the C6 and C4' positions of the structure. These variable substituents are defined such that X is selected from CH, N, S, and O, Y is selected from S, CO, NH, NO, and O, $R^1$ and optional $R^2$ are independently selected from H, OH, substituted or unsubstituted $C_1$-$C_6$ alkyl, substituted or unsubstituted $C_4$-$C_6$ cycloalkyl or cycloheteroalkyl, and aryl, $R^3$ is selected from H, OH, substituted or unsubstituted $C_1$-$C_6$ alkyl, and optional Z is selected from OH, $NH_2$, $NH(CO)R^4$, $NH(SO_2)R^4$, guanidine, alkylguanidine, and fluoroguanidine, $R^4$ is polyethylene glycol or substituted or unsubstituted $C_1$-$C_6$ alkyl group.

The method of using imidazopyridine derivatives also includes the use of pharmaceutically acceptable salts of the compounds encompassed by Formula I. The method also encompasses embodiments including the use of any of the subsets of imidazopyridine derivative described herein. In some embodiments, the compound of Formula I is administered together with a pharmaceutically acceptable carrier.

Cancer is a disease of abnormal and excessive cell proliferation. Cancer is generally initiated by an environmental insult or error in replication that allows a small fraction of cells to escape the normal controls on proliferation and increase their number. The damage or error generally affects the DNA encoding cell cycle checkpoint controls, or related aspects of cell growth control such as tumor suppressor genes. As this fraction of cells proliferates, additional genetic variants may be generated, and if they provide growth advantages, will be selected in an evolutionary fashion. Cells that have developed growth advantages but have not yet become fully cancerous are referred to as precancerous cells. Cancer results in an increased number of cancer cells in a subject. These cells may form an abnormal mass of cells called a tumor, the cells of which are referred to as tumor cells. The overall amount of tumor cells in the body of a subject is referred to as the tumor load. Tumors can be either benign or malignant. A benign tumor contains cells that are proliferating but remain at a specific site and are often encapsulated. The cells of a malignant tumor, on the other hand, can invade and destroy nearby tissue and spread to other parts of the body through a process referred to as metastasis.

Cancer is generally named based on its tissue of origin. There are several main types of cancer. Carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma and multiple myeloma are cancers that begin in the cells of the immune system. Examples of types of cancer that can be treated using the compounds of the present invention include cancer is selected from the group consisting of bladder cancer, prostate cancer, liver cancer, breast cancer, colon cancer, and leukemia.

In some embodiments, the cancer being treated is leukemia. Leukemia is a group of cancers that usually begin in the bone marrow and result in high numbers of abnormal white blood cells. These white blood cells are not fully developed and are called blasts or leukemia cells. Symptoms may include bleeding and bruising problems, feeling tired, fever, and an increased risk of infections. Types of leukemia include acute lymphoblastic leukemia, chronic lymphocytic leukemia, acute myeloid leukemia, chronic myeloid leukemia, T-cell prolymphocytic leukemia, and juvenile myelomonocytic leukemia.

In some embodiments, the leukemia being treated is acute myeloid leukemia (AML). AML is the most common acute leukemia affecting adults, and its incidence increases with age. The malignant cell in AML is the myeloblast. In normal hematopoiesis, the myeloblast is an immature precursor of myeloid white blood cells; a normal myeloblast will gradually mature into a mature white blood cell. In AML, though, a single myeloblast accumulates genetic changes which "freeze" the cell in its immature state and prevent differentiation. The symptoms of AML are caused by replacement of normal bone marrow with leukemic cells, which causes a drop in red blood cells, platelets, and normal white blood cells. These symptoms include fatigue, shortness of breath, easy bruising and bleeding, and increased risk of infection. Several risk factors and chromosomal abnormalities have been identified. As an acute leukemia, AML progresses rapidly and is typically fatal within weeks or months if left untreated.

The imidazopyridine derivatives of the invention can be used for both prophylactic and therapeutic treatment. When used for cancer treatment, the imidazopyridine derivatives can be referred to as anticancer, or antitumor agents. The imidazopyridine derivatives can, for example, be administered prophylactically to a mammal prior to the development of cancer. Prophylactic administration, also referred to as prevention, is effective to decrease the likelihood that cancer will develop in the subject. For prophylactic treatment, the subject is any human or animal subject, and preferably is a human subject who is at risk of acquiring a disorder characterized by unwanted, rapid cell proliferation, such as cancer. The subject may be at risk due to exposure to carcinogenic agents, being genetically predisposed to disorders characterized by unwanted, rapid cell proliferation, and so on.

Alternatively, imidazopyridine derivatives of the invention can, for example, be administered therapeutically to a subject that already has cancer. For purposes of treatment, a subject at risk includes any human or animal subject who has a disorder characterized by unwanted, rapid cell proliferation. Such disorders include, but are not limited to cancers and precancers. In one embodiment of therapeutic administration, administration of the imidazopyridine derivatives is effective to eliminate the cancer; in another embodiment, administration of the imidazopyridine derivatives is effective to decrease the symptoms or spread of the cancer.

The imidazopyridine derivatives of the invention can be used to treat cancer cells that have developed resistance to chemotherapy by traditional anticancer agents, such as antiproliferative or apoptosis-inducing agents. While not intending to be bound by theory, the imidazopyridine derivatives selectively induce p53-independent terminal differentiation in cancer cells such as acute myeloid leukemia cells, overcoming the differentiation failure that caused the cells to become cancerous. Accordingly, the imidazopyridine derivatives of the invention are particularly useful for treating cancer cells that result from a failure of the cells to differentiate. As a result of their mode of action, the imidazopyridine derivatives can also be referred to as differentiation-inducing agents suitable for carrying out differentiation therapy.

The effectiveness of cancer treatment may be measured by evaluating a reduction in tumor load or decrease in tumor growth in a subject in response to the administration of the imidazopyridine derivatives. The reduction in tumor load may be represent a direct decrease in mass, or it may be measured in terms of tumor growth delay, which is calculated by subtracting the average time for control tumors to grow over to a certain volume from the time required for treated tumors to grow to the same volume.

Candidate agents may be tested in animal models. Typically, the animal model is one for the study of cancer. The study of various cancers in animal models (for instance, mice) is a commonly accepted practice for the study of human cancers. For instance, the nude mouse model, where human tumor cells are injected into the animal, is commonly accepted as a general model useful for the study of a wide variety of cancers (see, for instance, Polin et al., Investig. New Drugs, 15:99-108 (1997)). Results are typically compared between control animals treated with candidate agents and the control littermates that did not receive treatment. Transgenic animal models are also available and are commonly accepted as models for human disease (see, for instance, Greenberg et al., Proc. Natl. Acad. Sci. USA, 92:3439-3443 (1995)). Candidate agents can be used in these animal models to determine if a candidate agent decreases one or more of the symptoms associated with the cancer, including, for instance, cancer metastasis, cancer cell motility, cancer cell invasiveness, or combinations thereof. In some embodiments, candidate anticancer agents can be detected using an in vitro assay system, such as the luciferase-based reporter assay for CEBPE promoter activity, described in Example 2 herein.

Methods of cancer treatment using the compounds described herein can further include the step of ablating the cancer. Ablating the cancer can be accomplished using a method selected from the group consisting of cryoablation, thermal ablation, radiotherapy, chemotherapy, radiofrequency ablation, electroporation, alcohol ablation, high intensity focused ultrasound, photodynamic therapy, administration of monoclonal antibodies, and administration of immunotoxins.

Methods of Stimulating Differentiation Using Imidazopyridine Derivatives

In another aspect, the present invention provides a method of stimulating differentiation in a cell, comprising contacting the cell with an effective amount of a compound according to formula I:

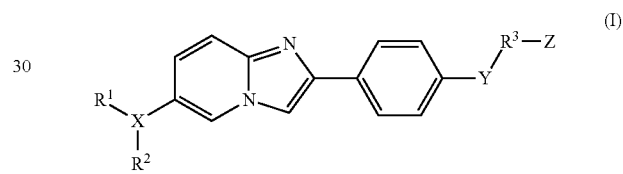

wherein X is selected from CH, N, S, and O, Y is selected from S, CO, NH, NO, and O, $R^1$ and optional $R^2$ are independently selected from H, OH, substituted or unsubstituted $C_1$-$C_6$ alkyl, substituted or unsubstituted $C_4$-$C_6$ cycloalkyl or cycloheteroalkyl, and aryl, $R^3$ is selected from H, OH, substituted or unsubstituted $C_1$-$C_6$ alkyl, and optional Z is selected from OH, $NH_2$, $NH(CO)R^4$, $NH(SO_2)R^4$, guanidine, alkylguanidine, and fluoroguanidine, $R^4$ is polyethylene glycol or substituted or unsubstituted $C_1$-$C_6$ alkyl, and pharmaceutically acceptable salt thereof.

Another aspect of the invention provides a method of stimulating differentiation in a cell, comprising contacting the cell with an effective amount of an imidazopyridine derivative according to formula I or a pharmaceutically acceptable salt thereof. As described herein, the compounds of the present invention have the ability to stimulate differentiation in cells such as cancer cells. Stimulating differentiation provides a useful unconventional strategy for cancer treatment that can be particularly useful for treating cancer that has become resistant to other treatment approaches.

The method involves contacting a cell with an imidazopyridine derivative. The cell can be contacted by the compound either in vivo or ex vivo. The cell can be an animal cell, such as a mammalian or human cell. The cell can be a healthy cell or it can be a diseased cell such as a cancer cell. The cell can be contacted by the compound as a result of the compound being added to the environment of the cell. The environment can be an artificial environment such as a tissue culture environment, or the cell can be in a natural environment such as being present within an animal. The compound contacts the cell by diffusion within the environment, and will be taken up or diffuse through the cell to contact SMARCA5 and thereby stimulate cell differentiation. The compound can be delivered by itself or in a pharmaceutical composition. Use of a pharmaceutical composition and methods of administration known to those skilled in the art is particularly useful for contacting a cell within a natural environment such as a subject.

Administration and Formulation

The present invention also provides pharmaceutical compositions that include imidazopyridine derivatives according to formula I as an active ingredient, and a pharmaceutically acceptable liquid or solid carrier or carriers, in combination with the active ingredient. Any of the compounds described above as being suitable for the treatment of cancer can be included in pharmaceutical compositions of the invention.

The imidazopyridine derivatives can be administered as pharmaceutically acceptable salts. Pharmaceutically acceptable salt refers to the relatively non-toxic, inorganic and organic acid addition salts of the imidazopyridine derivatives. These salts can be prepared in situ during the final isolation and purification of the imidazopyridine derivatives, or by separately reacting a purified imidazopyridine derivative with a suitable counterion, depending on the nature of the compound, and isolating the salt thus formed. Representative counterions include the chloride, bromide, nitrate, ammonium, sulfate, tosylate, phosphate, tartrate, ethylenediamine, and maleate salts, and the like. See for example Haynes et al., J. Pharm. Sci., 94, p. 2111-2120 (2005).

The pharmaceutical compositions includes one or more imidazopyridine derivatives together with one or more of a variety of physiological acceptable carriers for delivery to a patient, including a variety of diluents or excipients known to those of ordinary skill in the art. For example, for parenteral administration, isotonic saline is preferred. For topical administration, a cream, including a carrier such as dimethylsulfoxide (DMSO), or other agents typically found in topical creams that do not block or inhibit activity of the peptide, can be used. Other suitable carriers include, but are not limited to, albumin, alcohol, phosphate buffered saline, and other balanced salt solutions.

The formulations may be conveniently presented in unit dosage form and may be prepared by any of the methods well known in the art of pharmacy. Preferably, such methods include the step of bringing the active agent into association with a carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering to a subject, preferably a mammal, and more preferably a human, the composition of the invention in an amount effective to produce the desired effect. The imidazopyridine derivatives can be administered as a single dose or in multiple doses. Useful dosages of the active agents can be determined by comparing their in vitro activity and the in vivo activity in animal models. Methods for extrapolation of effective dosages in mice, and other animals, to humans are known in the art; for example, see U.S. Pat. No. 4,938,949.

The agents of the present invention are preferably formulated in pharmaceutical compositions and then, in accordance with the methods of the invention, administered to a subject, such as a human patient, in a variety of forms adapted to the chosen route of administration. The formulations include, but are not limited to, those suitable for oral, rectal, vaginal, topical, nasal, ophthalmic, or parental (including subcutaneous, intramuscular, intraperitoneal, intratumoral, and intravenous) administration.

Formulations of the present invention suitable for oral administration may be presented as discrete units such as tablets, troches, capsules, lozenges, wafers, or cachets, each containing a predetermined amount of the active agent as a powder or granules, as liposomes containing the imidazopyridine derivatives, or as a solution or suspension in an aqueous liquor or non-aqueous liquid such as a syrup, an elixir, an emulsion, or a draught. Such compositions and preparations typically contain at least about 0.1 wt-% of the active agent. The amount of protein imidazopyridine derivative (i.e., active agent) is such that the dosage level will be effective to produce the desired result in the subject.

Nasal spray formulations include purified aqueous solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, petroleum, polyhydroxy alcohols, or other bases used for topical pharmaceutical formulations.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, sugar, and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent may be incorporated into sustained-release preparations and devices.

Preparation of the Compounds

Compounds of the invention may be synthesized by synthetic routes that include processes similar to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie*, 4, Aufl. Ed. Springer-Verlag, Berlin, Germany, including supplements (also available via the Beilstein online database)).

Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

The present invention is illustrated by the following examples. It is to be understood that the particular examples, materials, amounts, and procedures are to be interpreted broadly in accordance with the scope and spirit of the invention as set forth herein.

EXAMPLES

Example 1

Novel Reporter Cell Line Measuring Promoter Activity of a Prominent Late-Differentiation Gene, CEBPE To identify new small molecules and druggable targets that mediate p53-independent cell cycle exit, the inventors have developed a novel reporter cell line measuring promoter activity of a prominent late-differentiation gene, CEBPE, in the AML cell line THP1. CEBPE is a key transcription factor that usually terminates proliferation of myeloid progenitors. Matsushita et al., Oncogene, 27(53): 6749-60 (2008). CEBPE is genetically intact in AML cells but often aberrantly epigenetically repressed. Negrotto et al., Leukemia, 26(2):244-54 (2012). This epigenetic repression is particularly intriguing since AML cells, including AML-initiating cells (leukemia stem cells), highly express the master differentiation-driving transcription factors CEBPA and PU.1 that usually activate CEBPE (FIG. 1A). Moreover, CEBPA and PU.1 can be localized at the CEBPE promoter. Gu et al., J Biol Chem., 289(21):14881-95 (2014). The inventors discovered that this paradox arises from alterations to binding partners for CEBPA/PU.1 such as RUNX1, such that corepressors instead of coactivators were recruited to late-differentiation gene loci. The screen was based on the idea that inhibiting these aberrantly recruited corepressors, either directly or indirectly, would promote coactivator binding to CEBPA/PU.1, CEBPE expression, and ultimately terminal differentiation (FIG. 1B).

Example 2

Screening for New Compounds Using the CEBPE Reporter Assay

Using the luciferase-based reporter assay for CEBPE promoter activity, the inventors screened the Specs diversity library of 46,000 drug-like molecules. The assay demonstrated a z'-factor of 0.8 during optimization and led to identification of approximately 500 hits that enhanced luciferase signal to at least the level of the positive control, the histone deacetylase inhibitor MS-275. Further validation of the hit list in secondary assays revealed a lead series, typified by ED2/ED3/ED43, that most strongly affected a range of differentiation phenotypes. The inventors validated ED2/3/43 as a small-molecule probes inducing differentiation in AML using the following 6 different assays, listed below, whose results are shown in FIG. 2:

1. Upregulation of CEBPE by Western Blot and reporter assay ($EC_{50}$ ca 3 µM).
2. Loss of proliferative capacity in AML cells without acute cytotoxicity or apoptosis.
3. No effect on viability of normal CD34+ HSCs, consistent with other inducers of differentiation.
4. Upregulation of the granulocyte cell surface markers CD11b and CD14.
5. Induction of granulocyte-specific morphological features by Giemsa staining.
6. Upregulation of CDKN1B/p27 levels (WB), indicative of cell cycle exit.

Induction of differentiation was observed across a small panel of AML cell lines, indicating general activity in AML (FIG. 3). Evaluation of newly synthesized ED2 in purity >95% provided near-identical effects on viability over 5 days as commercially available material, providing analytical validation of the assigned structure of ED2. Subsequent investigation identified multiple renal cell carcinoma cell lines in which ED2 reduced cell number at late time points without cytotoxicity at 2d and also induced morphological changes indicative of differentiation (FIG. 4). These results highlight that ED2's mechanism of action can induce differentiation in solid tumor-derived cells as well.

The inventors have also established that ED2 does not act by several established mechanisms known to modulate various differentiation processes (FIG. 5). No inhibition of the histone demethylases LSD1 and JMJD2A was observed, no binding to either bromodomain of BRD4 was observed, and no change in DNA methylation was observed after treatment of cells with ED2, eliminating DNA methyltransferase-mediated mechanisms. Importantly, the medicinal chemistry optimization of ED2 together with efforts to identify pharmacodynamic markers of activity using cell-line profiling and RNA-seq will facilitate target identification efforts. Potent and selective probes greatly improve the likelihood of identifying a molecular target using affinity chromatography, and the RNA-seq. data will provide insight into mechanism-of-action by identifying transcriptional pathways modulated by the inventors' optimized probe upstream of differentiation.

In addition to its well-validated cellular activity, ED2 represents a promising lead series for medicinal chemistry. The low molecular weight of this series (ED2 mol. wt.=253) and low number of rotatable bonds make this series 'lead-like' (Lipinski C A., Drug discovery today Technologies, 1(4):337-41 (2004)). Lead-like starting points allow for substantial addition of functional groups to enhance potency while maintaining 'drug-like' properties (e.g., mol. wt.<500 Da). Moreover, this scaffold bears similarity to zolpidem (Ambien) (FIG. 6), indicating that the core of ED2 likely has satisfactory in vivo pharmacology/safety.

Figure 6:
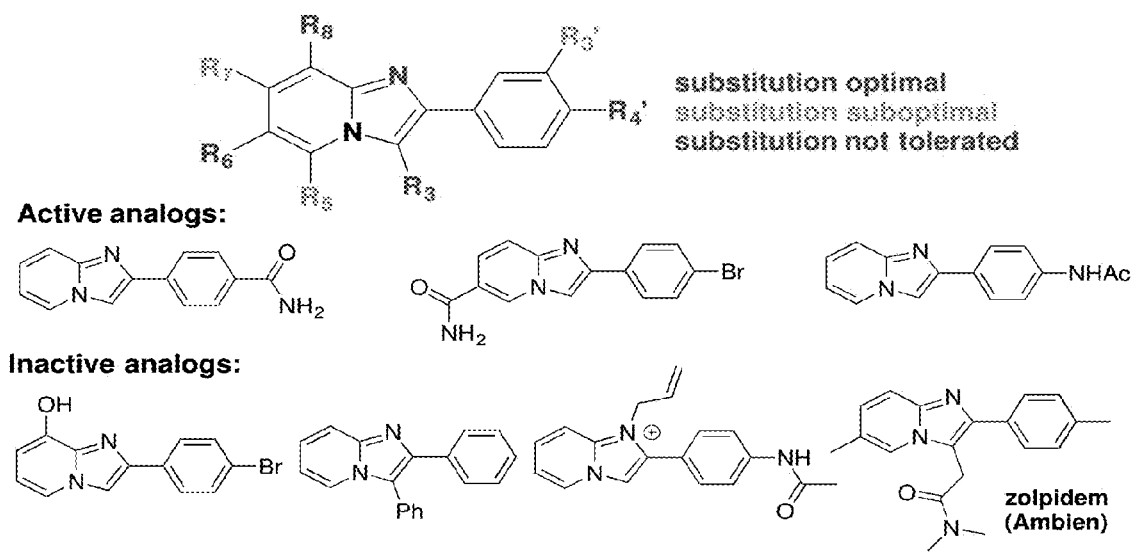
FIG. 6 provides a scheme showing a summary of initial SAR from screening of commercially available analogs.

To generate preliminary insights into structure-activity relationships (SAR), the inventors examined CEBPE-promoter activation in a panel of commercially-available ED2 analogs. This analysis, together with a review of additional imidazo[1,2-a]pyridines tested during the primary screen, defines clear structure-activity relationships (FIG. 6). The C6 and C4' positions are primed for further diversification using medicinal chemistry, several positions cannot be substituted, and others may tolerate limited substitution. Substitution at C3 as observed in zolpidem is generally not tolerated, consistent with our observation that zolpidem does not affect cell viability.

Figure 7:
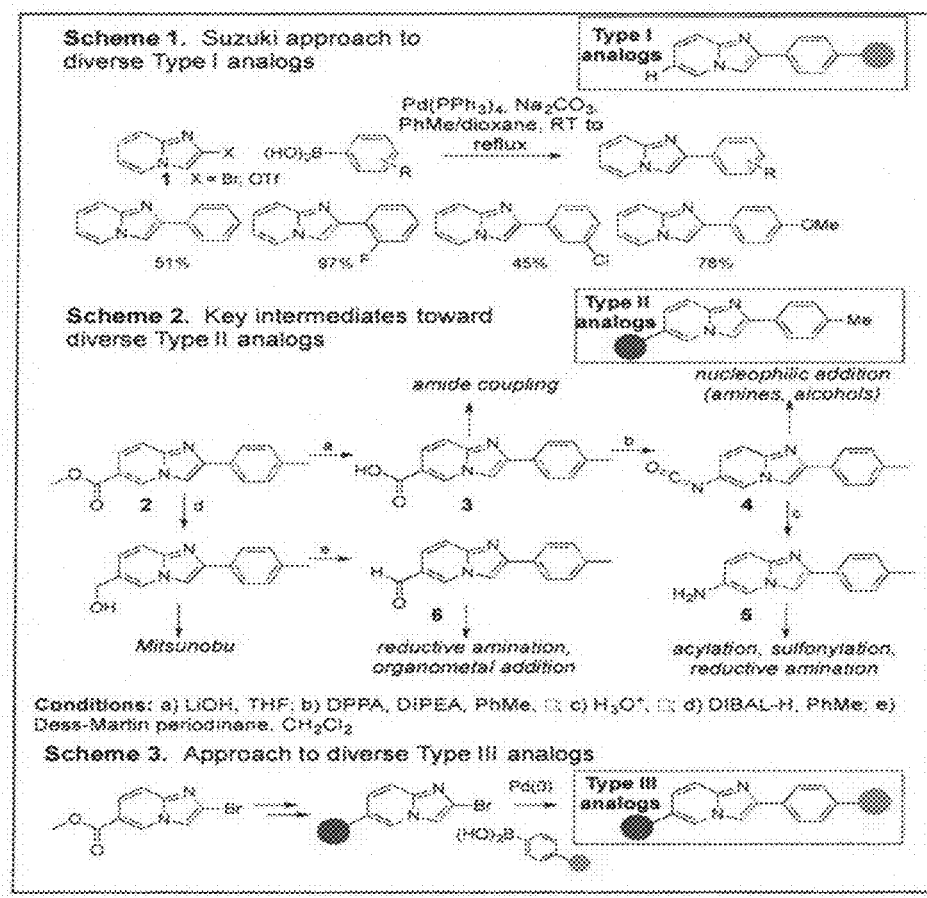
FIG. 7 provides schemes 1 through scheme 3 showing methods of synthesizing type I, type II, and type III analogs.

Preliminary analysis using commercially-available analogs identified two positions that are permissive to substitution (FIG. 6), and the inventors have explored diverse substituents at each of these sites. Type I analogs will modify the aromatic ring attached to the imidazo[1,2-a]pyridine heterocycle (Scheme 1). Schemes 1-3 are shown in FIG. 7. Type II analogs will replace the nitro substituent of ED2 (Scheme 2). Both analog types will be pursued in parallel to identify optimal potency enhancing substituents in each class. The simple, modular syntheses together with the validated assay tree maximize the speed and efficiency of chemical optimization. All combinations of leading C6 and C4' substituents will be synthesized to create Type III analogs that we predict will offer maximal potency (Scheme 3). These analogs, together with any Type I or Type II analogs with similar potency, will serve as starting points for further optimization of pharmacokinetic properties.

Figure 8:
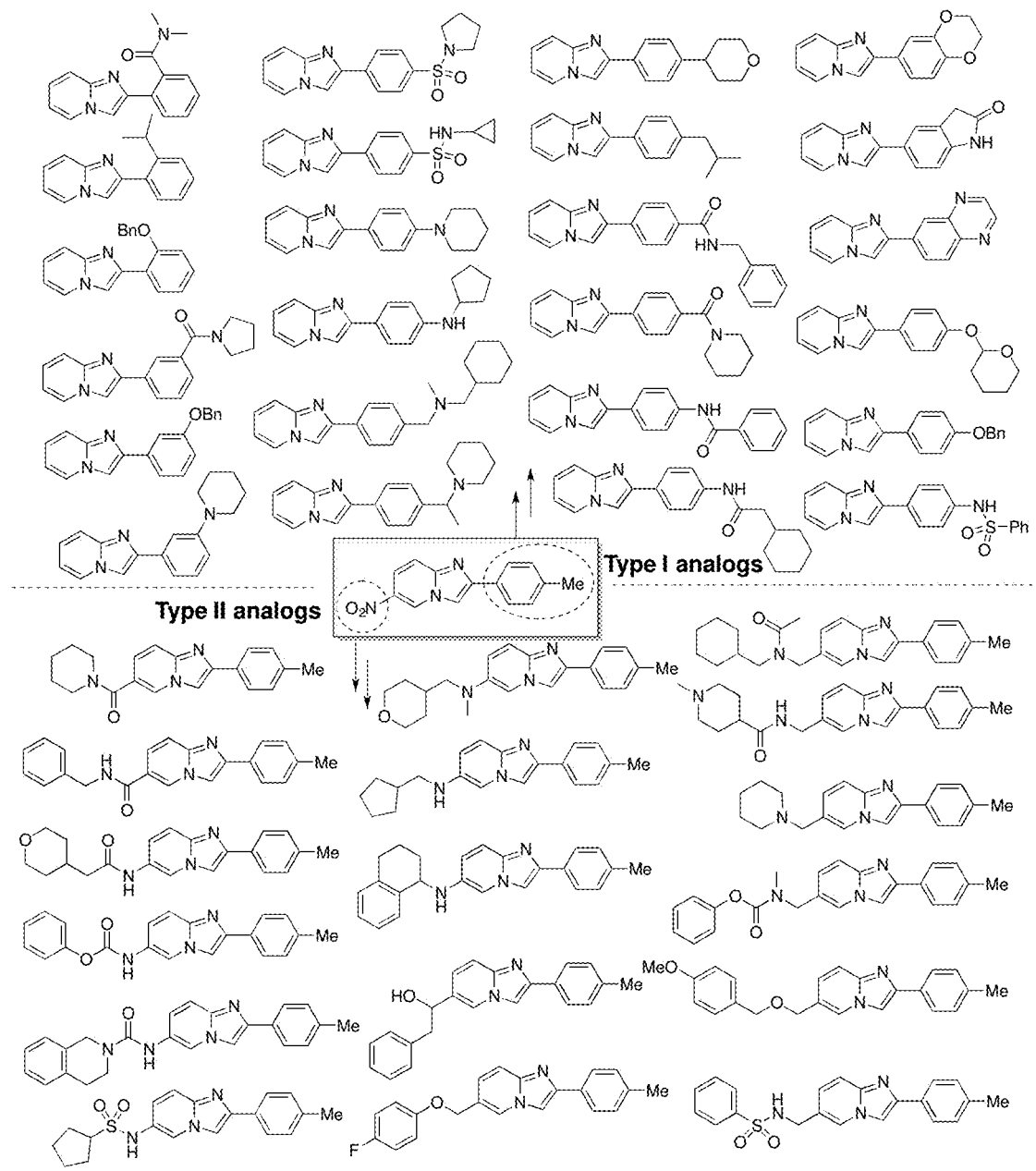
FIG. 8 provides the structures of proposed Type I and Type II analogs. Diverse substituents will be synthesized.

Type I analogs: A Pd-catalyzed Suzuki cross-coupling strategy provides a general approach to accessing Type I analogs in one step from commercially-available materials. This bond formation has been reported in several publications to proceed in moderate to excellent yield depending on the substitution pattern of the aryl boronic acid (Scheme 1). Marhadour et al., Eur J Med Chem., 58:543-56 (2012). Since substitution at C6 is unnecessary for activity (FIG. 6), the inventors began with commercially-available brominated analog 1. Using established procedures and commercially-available boronic acids/boronates, they will substitute the bromine atom with aryl groups bearing diverse substituents at the para-position (FIG. 8). Initial SAR indicates this position can be varied broadly, and the inventors will explore modifications that survey alkyl- and heteroatom-based substituents. No analogs with substitution at the ortho position have been tested to date, so diverse polar and nonpolar ortho-substituents will be synthesized to evaluate this position. Additionally, since some substituents at the meta position have retained activity, a smaller collection of 3-substituted or 3,4-disubstituted analogs will also be generated. A collection of structures under consideration that broadly survey potential substituents is given in FIG. 8; however, data from cellular evaluation of newly synthesized analogs will inform the choice of subsequent analogs.

Type II analogs: The inventors are optimizing the C6 position by surveying wide-ranging substituents. Initial SAR indicates carboxamide or anilide groups are tolerated (FIGS. 2 and 6), and we will initially diversify these functionalities. Starting with available ester 2, the inventors will derive acid 3 and undertake coupling with diverse primary and secondary amines (Scheme 2). Curtius arrangement of 3 will provide isocyanate 4, which can be captured directly using diverse nucleophiles or hydrolyzed to provide aniline 5. Substitution of the aniline will be pursued using standard reductive amination, acylation, and sulfonylation approaches. As a distinct approach, ester 2 will be reduced to aldehyde 6 and nucleophilic additions will be performed using simple alkyl metal reagents. Alternatively, reductive amination will be performed to provide a secondary amine, followed by an optional N-acylation or second reductive amination. As above, a collection of structures under consideration is given in FIG. 8.

Type III analogs: Type III analogs that combine a leading Type I substituent at C6 with a Type II substituent at C4' will be synthesized (Scheme 3). By using commercially-available bromo-ester 7 the inventors will prepare the desired C6 substituent as described in Scheme 2 and then complete the synthesis via Suzuki coupling of the aryl boronic acid containing the optimized C4' substituent. The Suzuki coupling will be achieved first. However, other synthesis approaches are possible as well. Each C6 or C4' substituent that shows >4-fold increase in potency will be included in the synthesis of Type III analogs and assessed in the cell-based assays. Combining two potency-enhancing substituents is expected to lead to Type III analogs with potency that meets or exceeds the goal of a 10-fold increase relative to ED2/3/43.

Example 3

Ability of Synthesized Probes to Overcome Differentiation-Arrest In Vivo

Figure 9:
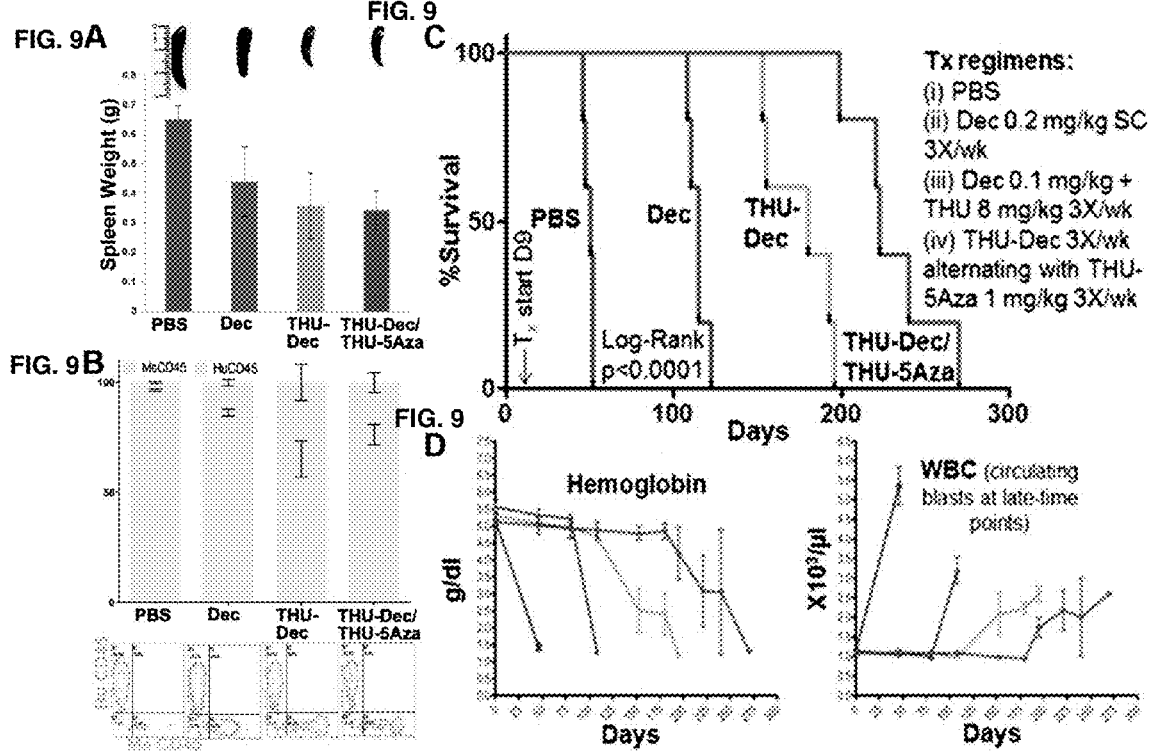
FIG. 9A-FIG. 9D provide graphs showing non-cytotoxic differentiation therapy enables chronic suppression of leukemia for strikingly extended periods of time in patient-derived xenotransplant models of AML. The deoxycytidine analogues decitabine (Dec) and 5-azacytidine (5Aza) were administered subcutaneously at dosages selected to deplete DNMT1 without DNA damage or cytotoxicity. THU inhibits an enzyme that metabolizes Dec and 5-aza, increases in vivo half-life of these agents, and enhances the S-phase dependent DNMT1-depleting therapeutic effects. Initial experiments euthanized all animals at the same time-point, when vehicle treated mice showed signs of distress. In those experiments, relative efficacy was determined by spleen weights and flow-cytometric evaluation of bone marrow leukemia burden (human CD45% versus murine Cd45%). Shown here are results for a confirmatory experiment that examined survival/latency, with euthanasia upon onset of anemia/distress. NSG mice (n=20) were xenotransplanted with one million primary human AML cells expanded by passage through NSG mice. A) Spleen weight at time of euthanasia (time-points per survival curve (panel C)). B) Flow-cytometric analysis of bone marrow for human leukemia (HuCD45) versus residual normal murine hematopoiesis (MsCd45). C) Kaplan-Meir curves. D) Blood counts.

The inventors have established xenotransplant models of various sub-types of primary human AML, including highest risk p53-null AML, that recapitulate the essential features of the human disease: infiltration of bone marrow and reticuloendothelial tissue by malignant cells, and fatality from cytopenia. Wunderlich et al., Blood, 121(12):e90-7 (2013), The feasibility and value of such experiments is illustrated in FIG. 9, which shows the results of experiments that evaluated a non-cytotoxic differentiation treatment strategy for AML that involves optimization of available drugs. Initial experiments will use cross-sectional analysis, with euthanasia of all mice when vehicle treated mice demonstrate signs of distress. Subsequently, the inventors will consider survival curve experiments, which can demonstrate the long-term safety and tolerance of non-cytotoxic epigenetic-differentiation treatments. Experiments will also include regular blood counts, again, to validate the non-cytotoxic, normal stem cell sparing mechanism of action of the probes. The dosing regimen will be determined according to in vivo pharmacokinetics data obtained through the Charles River Contract Research Organization (CRO), with the dose being chosen below to maintain plasma concentrations above the $EC_{50}$ between doses.

In addition to quantification of malignant burden and differentiation, end-points include measurement of molecular pharmacodynamic effect. Eighteen mice are inoculated with ~$1\times10^6$ patient-derived AML cells. Randomly selected mice (n=4) are sacrificed at day 14 to demonstrate pre-treatment tumor burden, then remaining mice are randomized to treatment with probe or vehicle to begin treatment on day 15 (n=7/group). If mice in either group demonstrate signs of distress (anticipated in the vehicle group at ~day 40), all mice are euthanized and tumor burden is quantified by blood counts, bone marrow human CD45 versus murine Cd45%, and spleen weights. Flow cytometry of human CD45+ cells will evaluate for differentiation induced in vivo. Additionally RNA will be isolated from human CD45+ cells and use RT-qPCR to assess levels of the small set of transcripts identified by the inventors to be robustly altered in response to probe treatment across multiple AML cell lines. Cells from probe- and vehicle-treated mice will be compared, and modulation of this gene set relative to a set of housekeeping genes and other transcripts not altered by probe treatment will indicate an on-target effect leading to differentiation.

The inventors believe that non-cytotoxic, AML differentiation-inducing probes, by sparing normal stem cells, lend themselves to chronic therapy. That is, probe therapy should suppress malignancy for extended periods without toxicity. To demonstrate this possibility, if cross-sectional experiments demonstrate meaningful activity, additional experiments will delay murine sacrifice in the treatment group until signs of distress (as illustrated in FIG. 9).

Example 4

Testing of 6-S Butyl ED2 Derivatives

Figure 10:
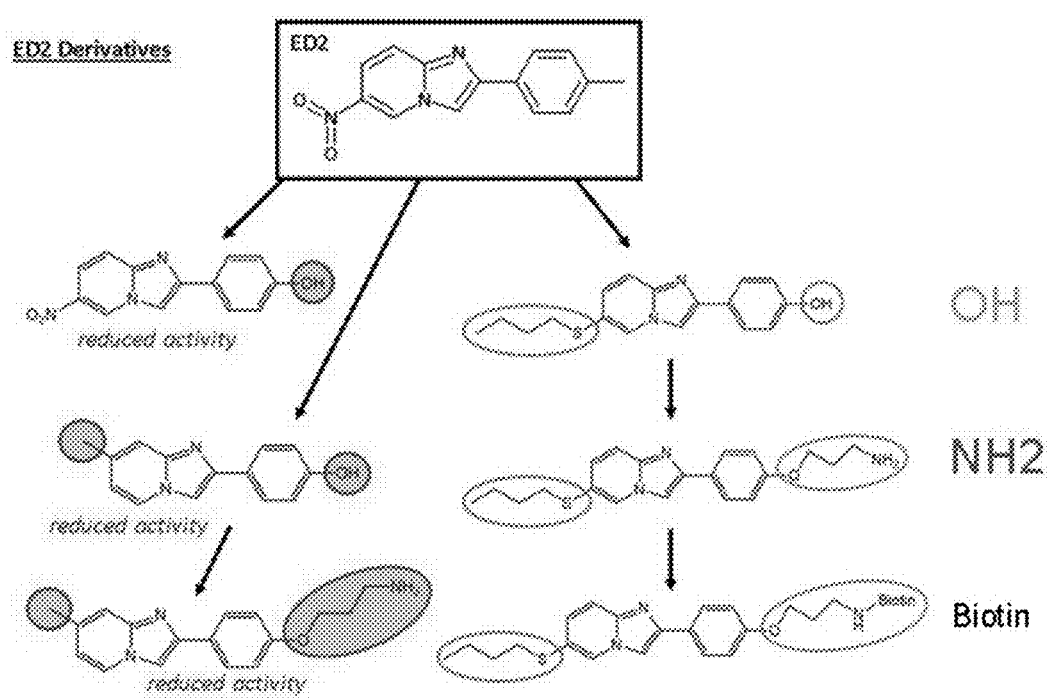
FIG. 10 provides a scheme showing three highly active 6-S butyl ED2 derivatives, as well as 3 compounds exhibiting reduced activity.
Figure 11:
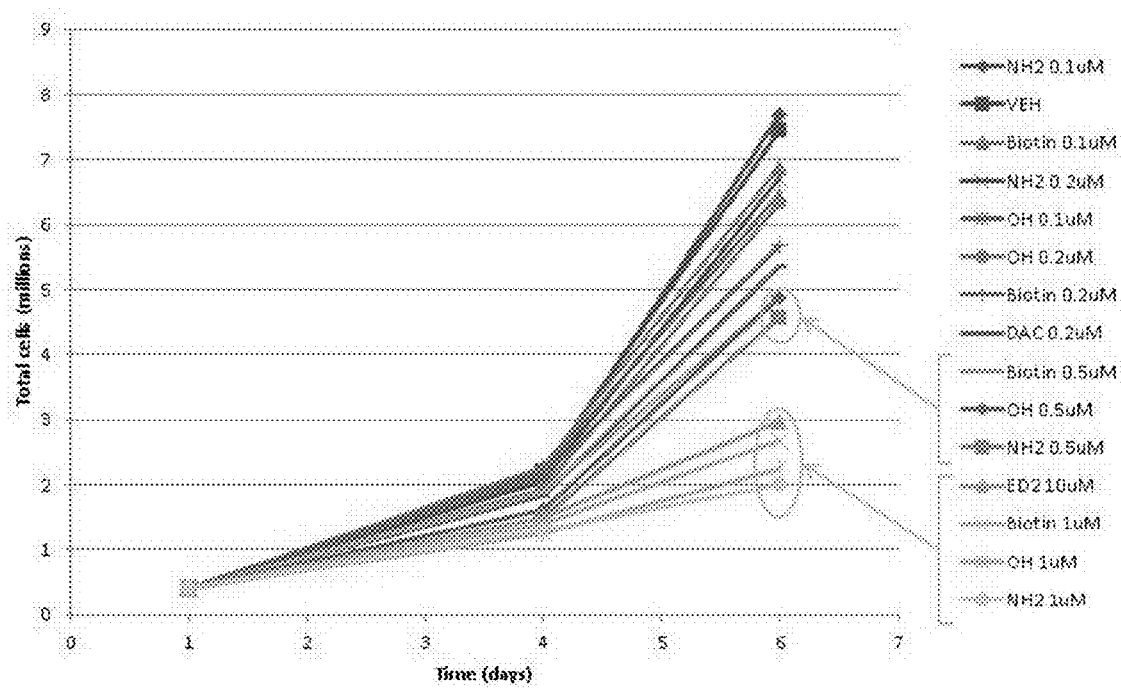
FIG. 11 provides a graph showing ED2 6-S butyl derivatives are more than 10 times more potent than the parent ED2 compound.
Figure 12A:
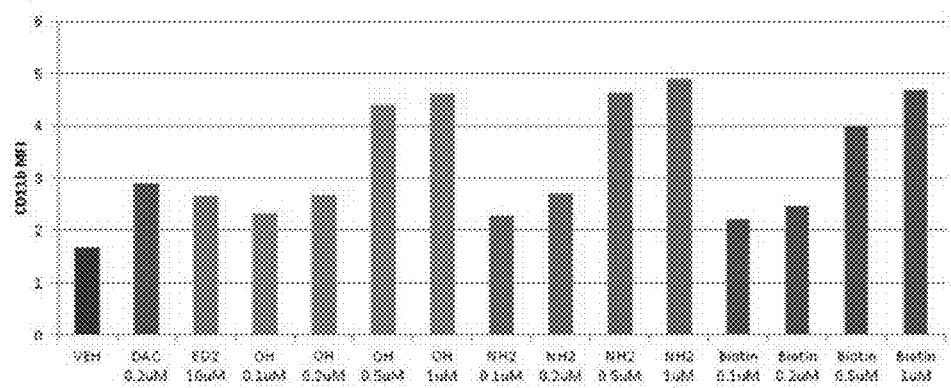
FIG. 12A and FIG. 12B show that 6-S butyl ED2 derivatives are better differentiation inducers than decitabine and ED2. (A) CD11b flow cytometry was performed on THP-1 cells 5 days after the indicated treatments. (B) Annexin-PI flow cytometry of the same cells to determine the percent of cells that were undergoing apoptosis after treatments with the different compounds. Camptothecin is a positive apoptosis inducer.
Figure 12B:
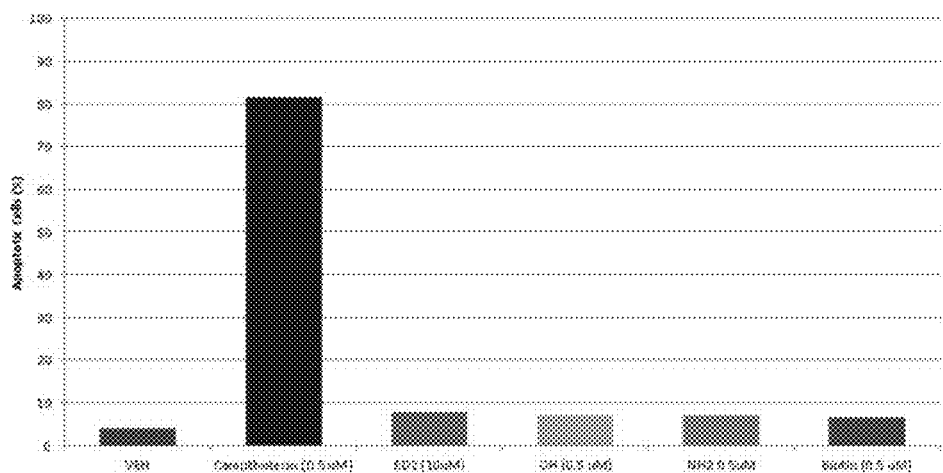

The inventors tested six derivatives of ED2, as shown in FIG. 10, and developed further insights into the structure-activity relationships of ED2 derivatives. The three structures shown on the right in FIG. 10 (designated OH, NH$_2$, and biotin) were all 6-S butyl ED2 derivatives that showed significantly improved activity. The three more active ED2 derivatives at 1 mM concentration show more potent growth inhibitory activity against THP-1 cells than the parent ED2 compound at 10 μM, as shown in FIG. 11. All three 6-S butyl ED2 derivatives are also better differentiation inducers than decitabine (DAC) and ED2, as evaluated via CD11b (a granulocyte differentiation cell surface marker) flow cytometry (FIG. 12A). These compounds also do not activate the apoptosis pathway (FIG. 12B).

Figure 13:
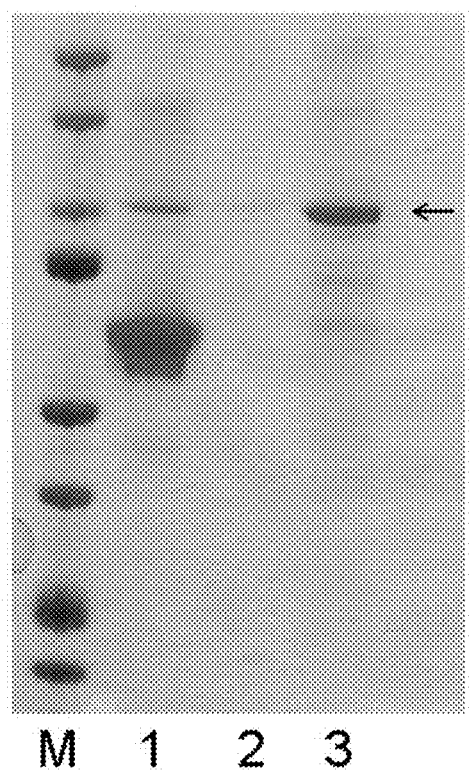
FIG. 13 provides an image showing ED2 binds the SMARCA5 Swi/Snf chromatin remodeler. The biotinylated ED2 derivative was used as bait to identify its potential molecular target. The image shows that ED2 binds to the purified SMARCA5. Lane M, molecular weight marker; lane 1, input, mixture of bovine serum albumin (BSA) and purified SMARCA5; lane 2, pull-down with streptavidin-agarose beads alone; lane 3, pull-down with ED2-loaded streptavidin beads. Arrowhead indicated the position of SMARCA5.

To facilitate the creation and design of new derivatives, the inventors sought to identify the molecular target of ED2. A biotinylated derivative of ED2 was synthesized to allow attachment of the drug to a solid matrix (streptavidin agarose) for use in affinity chromatography studies (FIG. 13). Based on design of the initial drug screening protocol and its broad pan-cancer activity, the inventors hypothesized that ED2's molecular target is an epigenetic modifier capable of silencing the plethora of terminal differentiation drivers in all the different cancer subtypes that it has shown activity against. To that end, the inventors focused their search on epigenetic modifiers and now have evidence that ED2 binds to the catalytic core of SMARCA5, a component of Swi/Snf nucleosome remodeling complex found in both eukaryotes and prokaryotes. FIG. 13 shows direct binding of the ED2 compound to the catalytic ATPase core of recombinant human SMARCA5.

Figure 14A:
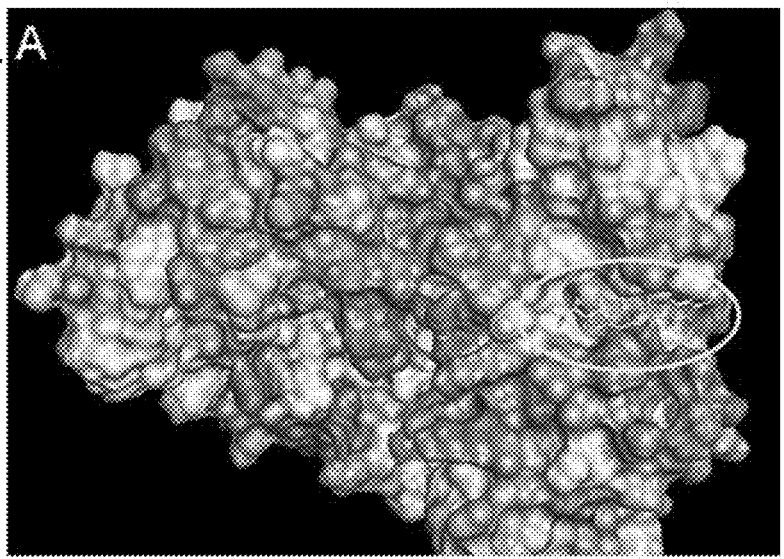
FIG. 14A and FIG. 14B provide images showing a molecular model of ED3 interacting with the catalytic core of human SMARCA5 Swi/Snf chromatin remodeler. A) a 3D surface plot showing ED3 binding to a pocket on the surface of SMARCA5 that is adjacent to the ATPase catalystic site. B) Molecular docking simulations and 3DQSAR (quantitative structure-activity relationship) modeling identified two positions amenable to modifications that would increase the binding specificity and solubility of ED2. The hydrophobic groups at point 1 and the polar group at point 2 will enhance the affinity and selectivity of the compounds for SMARCA5. Any functional group that can form a (i) salt bridge (ii) hydrogen bond can be used at point 2.
Figure 14B:
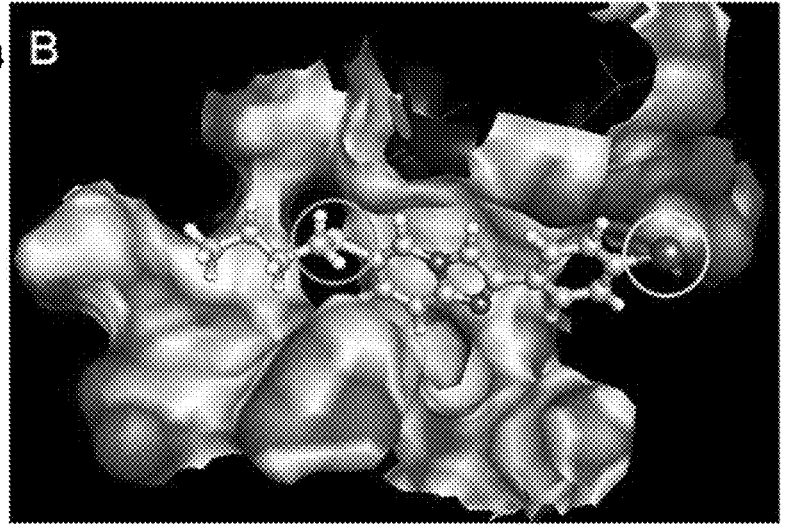

From these findings, the next generation design of ED2 analogs has been further developed based on structure guided by field-based free energy perturbation (FEP) molecular docking simulations and 3DQSAR of ED2 binding to the catalytic core of SMARCA5 (FIG. 14A). Using FEP and docking simulation, the inventors have designed several additional compounds. Based on the analysis (FIG. 14B), two sites of the molecule are being optimized. One site will be substituted with hydrophobic groups (2-6 carbon, including alicyclic, FIG. 14B), while the other site (point 2) should have polar/charged substituents that can potentially be exploited for developing pharmacological formulations (FIG. 14B). Adding PEG/—COOH/—OH/—CHO to this position will improve the solubility of the compound in aqueous solution, an important parameter to increase the changes of an active molecule in later in-vivo animal model and human studies.

Example 5

ED2 is Pan-Cancer Active

Figure 15A:
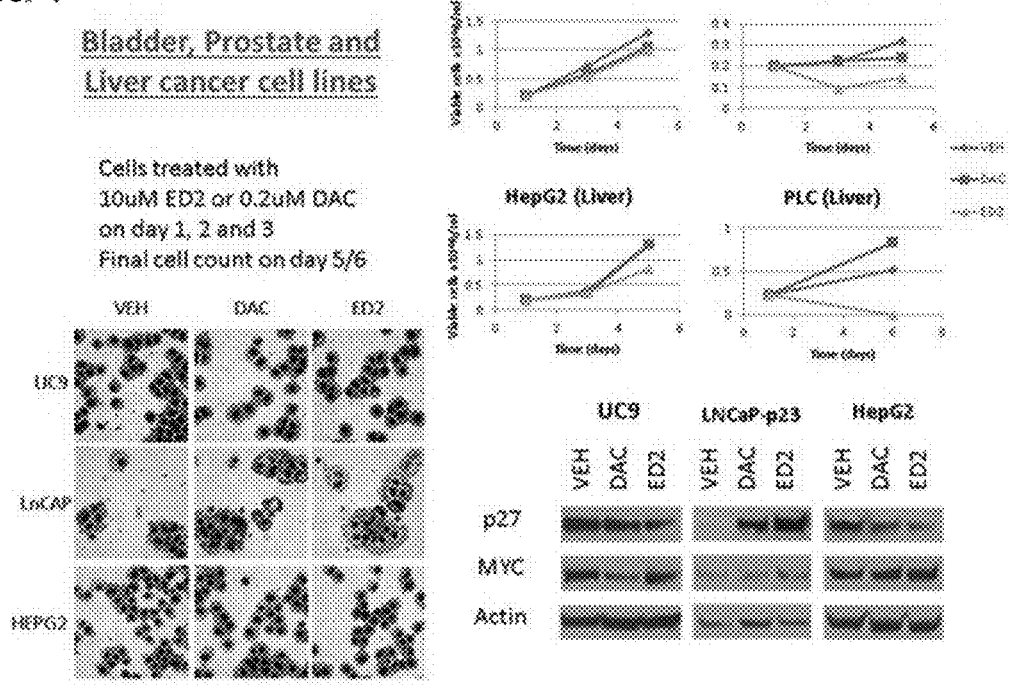
FIG. 15A-FIG. 15D provides graphs and images showing that ED2 is active against a variety of different types of cancer. The differentiation inducing activities of ED2 were evaluated against a wide variety of solid cancers such as bladder, prostate, and liver (A), breast cancer (B), lung and colon cancer (C), and multiple myeloma (D). ED2 activity for each of the different cancers were evaluated by determining the cell growth suppression (top right of each panel), morphological changes—increase in cytoplasmic to nuclear ratio is indicative of cellular differentiation (bottom left of each panel).
Figure 15B:
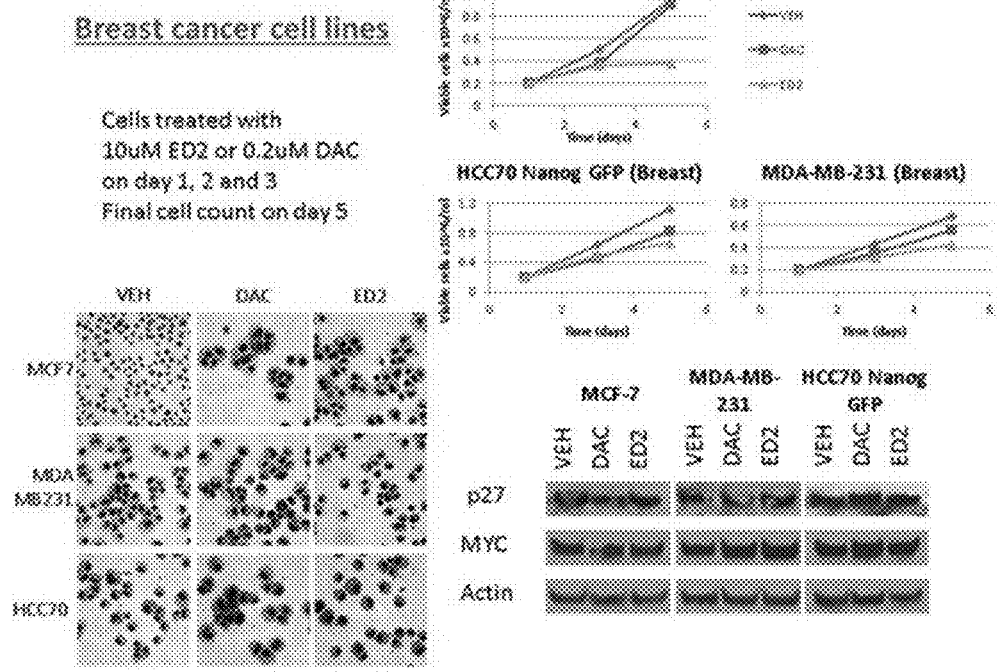
Figure 15C:
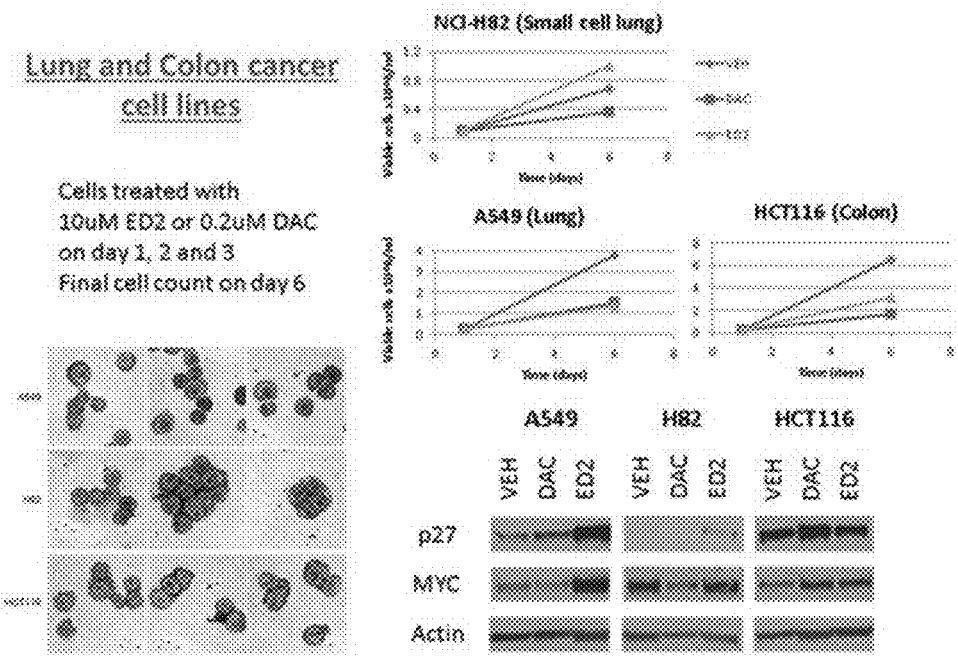
Figure 15D:
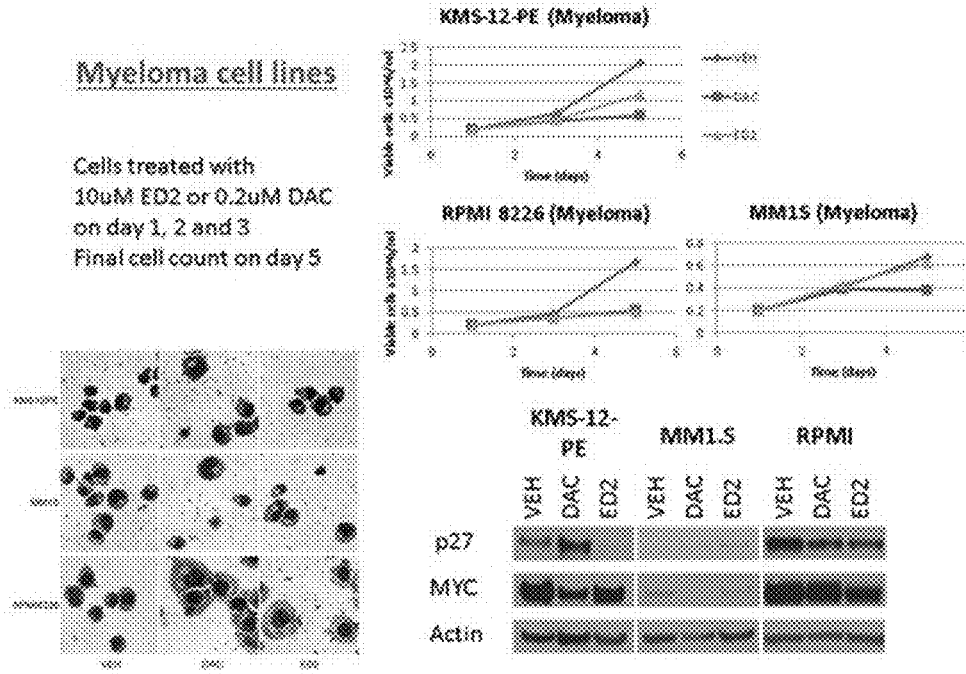

The inventors have tested ED2 against a wide variety of cancers, including solid tumors such as bladder, prostate, liver, breast, lung, and colon cancers, as well as multiple myeloma (see FIGS. 15A-15D). The only cancer cell line that ED2 had little or no effect on was NCI-H82, a small cell lung cancer (FIG. 15C) and MM1.S multiple myeloma cells (FIG. 15D).

Example 6

Preparation of 6-S Butyl ED2 Derivatives

Figure 16:
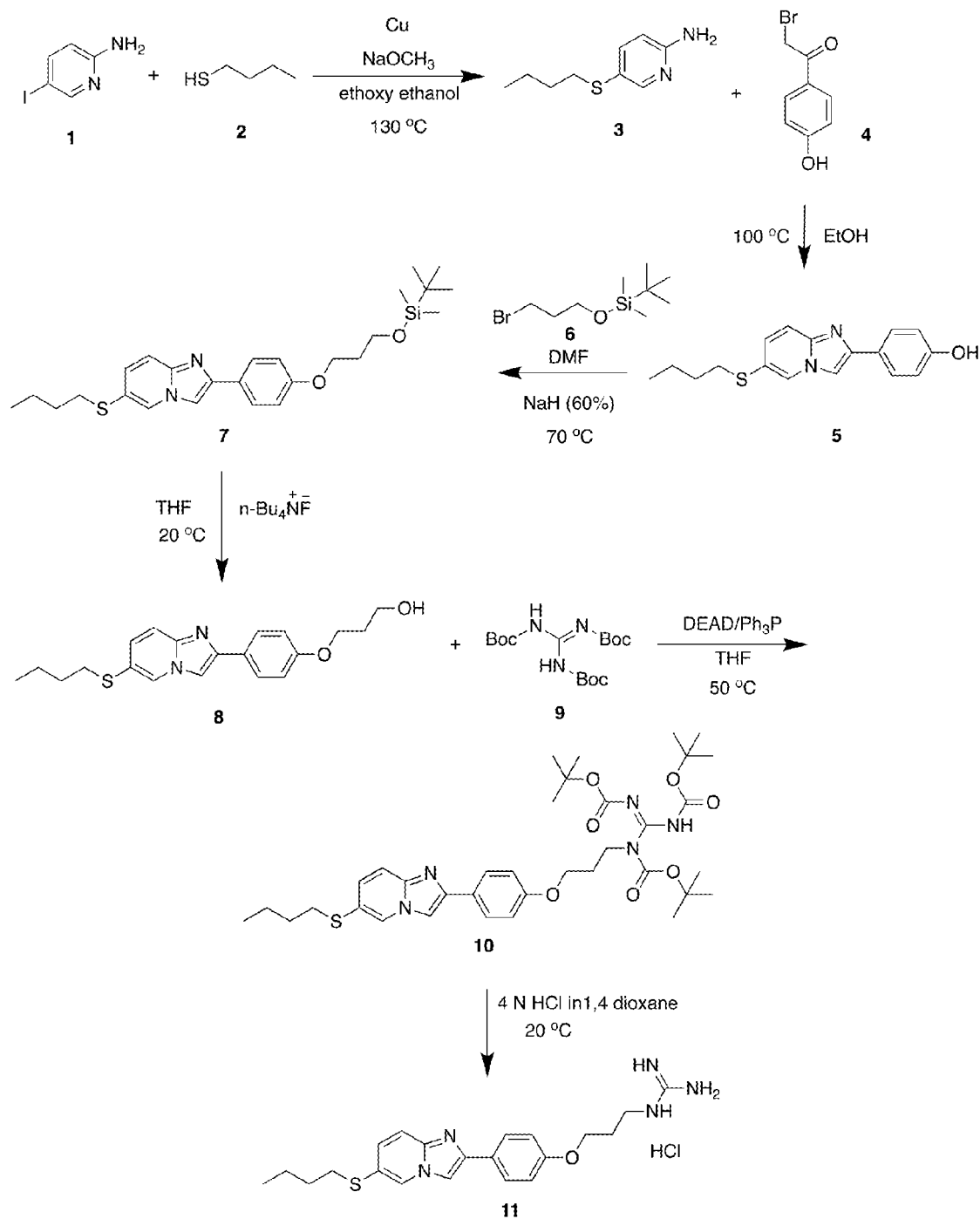
FIG. 16 provides a scheme for synthesizing 1-(3-(4-(6-(butylthio)imidazo[1,2-a]pyridine-2-yl)phenoxy)propyl)guanidine hydrochloride.

A method for synthesizing 1-(3-(4-(6-(butylthio)imidazo[1,2-a]pyridine-2-yl)phenoxy)propyl)guanidine hydrochloride is shown in FIG. 16, and is described below.

Synthesis of 5-(butylthio)pyridin-2-amine (3): A suspension of Cu powder (1.0 g), NaOCH$_3$ (20 mL, 68.46 mmol, 25% in Methanol, d=0.72 g/mL), 1-Butanethiol (7.1 mL, 70.1 mmol, d=0.84 g/mL) and 2-amino-5-iodopyridine (10.0 g, 44.73 mmol) in 50 mL of 2-ethoxyethanol refluxed at 130° C. for 24 h. After completion of reaction, monitored by TLC, reaction mixture was cooled and filtered through celite. The filtrate was concentrated and the crude partitioned between 100 mL water and 100 ml ethyl acetate. The aqueous layer was extracted 3 times (100 mL each) with ethyl acetate, the organic extracts combined and washed with brine (100 mL), dried over the MgSO$_4$, filtered, and concentrated to give a black oil (8.0 g, 90%). This was used for the next step without further purification.

$^1$H NMR (500 MHz, Chloroform-d) δ 8.16 (d, J=2.3 Hz, 1H), 7.54 (dd, J=8.5, 2.3 Hz, 1H), 6.47 (d, J=8.5 Hz, 1H), 4.56 (brs, 2H), 2.74 (t, J=7.4 Hz, 2H), 1.60-1.50 (m, 2H), 1.41 (q, J=7.4 Hz, 2H), 0.90 (t, J=7.4 Hz, 3H). $^{13}$C NMR (126 MHz, CDCl$_3$) δ 157.8, 152.5, 143.1, 120.4, 108.9, 36.7, 31.6, 21.8, 13.8.

Synthesis of 4-(6-(butylthio)imidazo[1,2-a]pyridin-2-yl)phenol (5): A solution of compound 3 (3.7 g, 16.24 mmol) and 2-Bromo-4'-hydroxyacetophenone 4 (3.5 g, 16.24 mmol) in anhydrous ethanol (100 mL) was refluxed for 24 h. After the completion of reaction, monitored by TLC, reaction mixture was cooled to rt and ethanol was removed under reduced pressure. The crude product was suspended in crushed ice and left stirring overnight. The off white precipitate formed was filtered on Buchner funnel under vacuum, washed with water (5×30 ml) and once with 20% ethyl acetate: hexane (50 mL). After drying 7.5 g (90% yield) of compound 5 was obtained and used as such for next step.

$^1$H NMR (500 MHz, DMSO-d$_6$) δ 10.16 (s, 1H), 8.90 (s, 1H), 8.55 (d, J=2.2 Hz, 1H), 7.92-7.85 (m, 2H), 7.78 (d, J=8.3 Hz, 2H), 6.99 (d, J=8.4 Hz, 2H), 3.08 (t, J=7.3 Hz, 2H), 1.66-1.54 (m, 2H), 1.50-1.38 (m, 2H), 0.90 (t, J=7.3 Hz, 3H).

Synthesis of 2-(4-(3-((tert-butyldimethylsilyl)oxy)propoxy)phenyl)-6-(butylthio)imidazo[1,2-a]pyridine (7): To compound 5 (2.5 g, 8.0 mmol) dissolved in dry DMF (20 mL) at 0° C. was added NaH portionwise (60% in mineral oil, 0.40 g, 9.0 mmol). The reaction mixture was stirred for 1 h. (3-Bromopropoxy)-tert-butyldimethylsilane 6 (2.8 g 11.0 mmol) was added and the reaction mixture heated at 70° C. for 12 h with continuous stirring. After completion of reaction, monitored by TLC, the reaction was quenched with water (60 ml) and extracted with ethyl acetate (5×50 mL). The combined organic extracts were washed with brine (3×50 mL), separated, and dried over MgSO$_4$, and filtered. The filtrate was concentrated and the crude product purified by flash silica column chromatography eluting with 30% ethyl acetate/70% hexanes to give 1.9 g of 7 (50% yield).

$^1$H NMR (500 MHz, Chloroform-d) δ 8.18 (s, 1H), 7.85 (d, J=9.6 Hz, 2H), 7.73 (s, 1H), 7.57 (d, J=9.6 Hz, 1H), 7.22 (d, J=9.2 Hz, 1H), 6.97 (d, J=8.8 Hz, 2H), 4.11 (t, J=6.2 Hz, 2H), 3.82 (t, J=6.0 Hz, 2H), 2.85 (t, J=7.4 Hz, 2H), 2.00 (p, J=6.1 Hz, 2H), 1.59 (p, J=7.3 Hz, 2H), 1.44 (h, J=7.4 Hz, 2H), 0.91 (t, J=7.4 Hz, 3H), 0.89 (s, 9H), 0.05 (s, 6H). $^{13}$C NMR (126 MHz, CDCl$_3$) δ 159.3, 146.2, 144.5, 129.2, 127.3, 127.3, 125.9, 120.3, 117.0, 114.8, 107.1, 64.5, 59.5, 35.6, 32.4, 31.4, 25.9, 21.7, 18.3, 13.6, −5.3.

Synthesis of 3-(4-(6-(butylthio)imidazo[1,2-a]pyridin-2-yl)phenoxy)propan-1-ol (8): To compound 7 (1.9 g, 4.04 mmol) dissolved in dry THF (50 mL) at rt was added N-tetrabutylammonium fluoride solution (8.1 mL, 1.0 M in THF). After completion of reaction, monitored by TLC, the solvent was evaporated under reduced pressure. Water was added (50 ml) and the mixture was extracted with ethyl acetate (4×50 mL). The combined organic layers were separated, dried over $MgSO_4$, filtered, and concentrated. The crude product was purified by silica flash column chromatography eluting with 80% ethyl acetate/20% hexanes, which provided 1.0 g (75% yield) of 8.

$^1$H NMR (500 MHz, Chloroform-d) δ 8.17 (t, J=1.3 Hz, 1H), 7.89-7.84 (m, 2H), 7.54 (d, J=9.3 Hz, 1H), 7.21 (dd, J=9.3, 1.7 Hz, 1H), 7.00-6.89 (m, 2H), 4.17 (t, J=6.0 Hz, 2H), 3.89 (t, J=5.9 Hz, 2H), 2.84 (dd, J=8.2, 6.6 Hz, 2H), 2.07 (p, J=6.1 Hz, 2H), 1.63-1.54 (m, 2H), 1.43 (q, J=7.4 Hz, 2H), 0.91 (t, J=7.4 Hz, 3H). $^{13}$C NMR (126 MHz, $CDCl_3$) δ 159.1, 146.3, 144.7, 129.4, 127.5, 127.4, 126.4, 120.4, 117.2, 114.9, 107.4, 65.9, 60.6, 60.5, 35.7, 32.2, 31.5, 21.9, 13.8.

Synthesis of 3-(4-(6-(butylthio)imidazo[1,2-a]pyridin-2-yl)phenoxy)propan amine tri-boc Guanadine (10): A solution of compound 8 (0.250 g, 0.70 mmol), N,—N'-N"-tri-Boc-guanadine (1.26 g, 3.51 mmol) and triphenyl phosphine ($Ph_3P$, 0.275 g, 1.05 mmol) in anhydrous THF (50 mL) was cooled to 5° C. under $N_2$. Diethylazodicarboxylate (DEAD, 0.18 mL, 1.05 mmol, d=1.1 g/mL) was added dropwise at a rate such that the reaction mixture was completely colorless before addition of the next drop. After the addition of DEAD, the reaction mixture was stirred for 18 h at 50° C. After completion of reaction, monitored by TLC, the reaction mixture was cooled to rt and hexanes (50 mL) added. A precipitate of excesses N,—N'-N"-tri-Boc-guanadine forms which is separated by the filtration on Buchner funnel and washed with mixture of THF:hexanes (1:1, 50 mL). The filtrate is concentrated under reduced pressure and the crude product (light yellow sticky solid, 0.040 g was purified by flash column chromatography on silica gel (eluent: 30% ethyl acetate/70% hexanes).

$^1$H NMR (500 MHz, Chloroform-d) δ 8.11 (s, 1H), 7.78 (d, J=8.6 Hz, 2H), 7.65 (s, 1H), 7.57-7.48 (m, 1H), 7.16 (d, J=9.7 Hz, 1H), 6.90-6.86 (m, 2H), 4.03 (t, J=6.2 Hz, 2H), 3.96 (t, J=6.9 Hz, 2H), 2.78 (t, J=7.4 Hz, 2H), 2.10 (t, J=6.6 Hz, 2H), 1.52 (q, J=7.6 Hz, 3H), 1.44 (s, 4H), 1.42 (s, 16H), 1.40 (s, 9H), 1.19 (s, 5H), 0.85 (t, J=7.4 Hz, 3H). $^{13}$C NMR (126 MHz, $CDCl_3$) δ 159.4, 153.6, 152.8, 127.5, 127.2, 114.9, 107.2, 83.51, 65.6, 45.2, 35.6, 31.5, 29.8, 28.7, 28.2, 28.', 28.1, 21.9, 13.7.

1-(3-(4-(6-(butylthio)imidazo[1,2-a]pyridin-2-yl)phenoxy)propyl)guanidine hydrochloride (11): To compound 10 (0.040 g) was added 4.0 N HCl in dioxane (10 mL). The reaction mixture was stirred at 20° C. for 4 h. After completion of reaction, the solvent were evaporated under reduced pressure on rotatory evaporator and residue was dissolved in diethyl ether (10 mL). The ether was allowed to evaporate slowly in the fume hood, which gave the HCl salt 11, 0.020 g (70%).

$^1$H NMR (500 MHz, Methanol-$d_4$) δ 8.71 (s, 1H), 8.36 (s, 1H), 7.89 (d, J=9.2 Hz, 1H), 7.85 (d, J=3.7 Hz, 2H), 7.81 (d, J=9.2 Hz, 1H), 7.18 (dd, J=17.4, 8.3 Hz, 2H), 3.60 (d, J=4.8 Hz, 2H), 3.43-3.37 (m, 2H), 3.08 (t, J=7.3 Hz, 2H), 2.11 (p, J=6.4 Hz, 2H), 1.67 (q, J=7.4 Hz, 2H), 1.50-1.46 (m, 2H), 0.95 (t, J=7.4 Hz, 3H).

Figure 17:
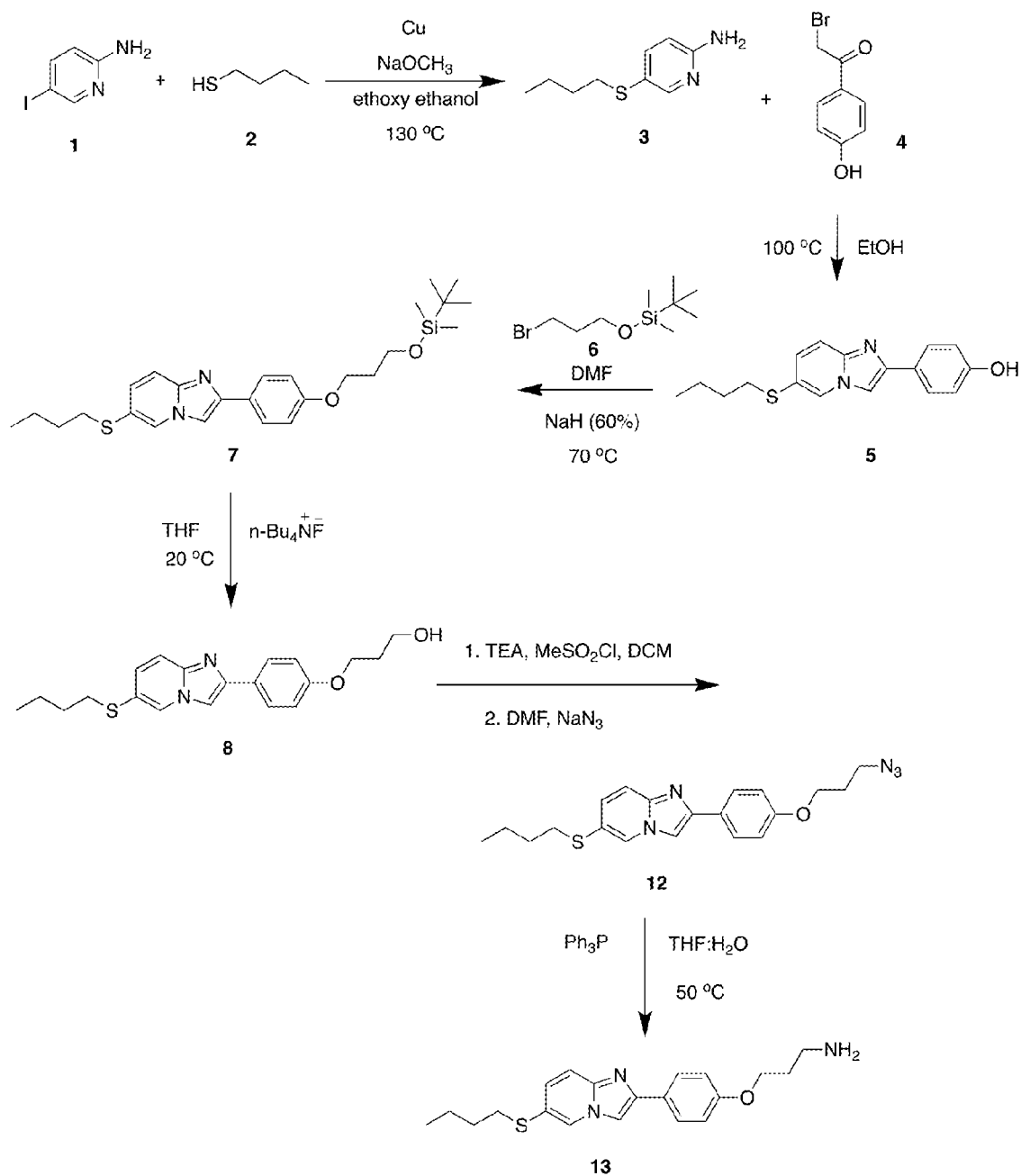
FIG. 17 provides a scheme for synthesizing 3-(4-(6-butylthio)imidazo[1,2-a]pyridine-2-yl)phenoxy)propan-1-amine.

A method for synthesizing 3-(4-(6-butylthio)imidazo[1,2-a]pyridine-2-yl)phenoxy)propan-1-amine is shown in FIG. 17, and is described below.

2-(4-(3-azidopropoxy)phenyl)-6-(butylthio)imidazo[1,2-a]pyridine (12): To compound 8 (0.8 g, 2.24 mmol) dissolved in dry dichloromethane (DCM, 20 mL) at rt, was added triethylamine (TEA, 0.4 mL, d=0.72 g/mL, 3.4 mmol). The reaction mixture was cooled to 0° C. followed by the addition of methanesulfonyl chloride (0.2 mL, 2.69 mmol, d=1.48 g/mL) and stirring continued for 2 h. After completion of reaction, monitored by TLC, the reaction was quenched with water (50 mL) and extracted with ethyl acetate (3×50 mL). The combined organic extracts were washed with brine (50 mL), separated, dried over $MgSO_4$, and filtered. This intermediate was used for the next step without purification and characterization. To this intermediate (0.80 g, 1.84 mmol) dissolved in dry DMF (20 mL) was added sodium azide (0.50 g, 7.36 mmol). Reaction mixture was heated at 50° C. for 12 h. After completion of reaction, monitored by TLC, the reaction was quenched with water (50 mL) and extracted with ethyl acetate (5×50 mL). The combined organic extracts were washed with brine (5×50 mL), separated, dried over $MgSO_4$, and filtered. The filtrate was concentrated and the crude product was purified by the flash silica chromatography eluting with 20% ethyl acetate/ 80% hexane to give 12, 0.180 g (80%) as a yellow sticky solid.

$^1$H NMR (500 MHz, Chloroform-d) δ 8.18 (s, 1H), 7.87 (d, J=8.4 Hz, 2H), 7.73 (s, 1H), 7.56 (d, J=9.3 Hz, 1H), 7.22 (dd, J=9.3, 1.6 Hz, 1H), 6.97 (d, J=8.3 Hz, 2H), 4.10 (t, J=5.9 Hz, 2H), 3.54 (t, J=6.7 Hz, 2H), 2.85 (t, J=7.4 Hz, 2H), 2.08 (q, J=6.3 Hz, 2H), 1.64-1.53 (m, 2H), 1.43 (q, J=7.4 Hz, 2H), 0.91 (t, J=7.3 Hz, 3H).

3-(4-(6-(butylthio)imidazo[1,2-a]pyridin-2-yl)phenoxy)propan-1-amine (13):

To compound 12 (0.180 g, 0.47 mmol) dissolved in THF was added triphenylphosphine (0.40, 1.42 mmol) and reaction mixture was heated at 50° C. for 1 h. 5 equivalents of water was added and the reaction continued for 3 more hr. After completion of reaction, monitored by TLC, the solvent was evaporated under reduced pressure. Water was added to the crude mixture, and pH was adjusted to 10.0 with aqueous NaOH solution (10% w/v). The mixture A precipitate was extracted with ethyl acetate (3×50 mL). The combined extracts were washed with brine (50 mL), dried over $MgSO_4$, and filtered. The filtrated was concentrated under reduced pressure to give the final product 13 (0.040 g, 20%).

$^1$H NMR (500 MHz, Methanol-d4) δ 8.20 (s, 1H), 7.78-7.75 (m, 2H), 7.47 (d, J=9.3 Hz, 2H), 7.23 (d, J=9.3 Hz, 1H), 6.94 (d, J=8.4 Hz, 2H), 2.90 (t, J=7.0 Hz, 2H), 2.83 (t, J=7.4 Hz, 2H), 2.00-1.93 (m, 2H), 1.60-1.51 (m, 2H), 1.44-1.37 (m, 2H), 0.88 (t, J=7.4 Hz, 3H).

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A compound of formula I

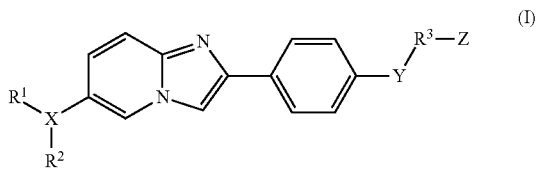

wherein X is S, Y is selected from S, CO, NH, NO, and O, $R^1$ is butyl and optional $R^2$ is selected from H, OH, substituted or unsubstituted $C_1$-$C_6$ alkyl, substituted or unsubstituted $C_4$-$C_6$ cycloalkyl or cycloheteroalkyl, and aryl;

$R^3$ is selected from H, OH, substituted or unsubstituted $C_1$-$C_6$ alkyl, and optional Z is selected from OH, $NH_2$, NH(CO)$R^4$, NH($SO_2$)$R^4$, guanidine, alkylguanidine, and fluoroguanidine, $R^4$ is polyethylene glycol or substituted or unsubstituted $C_1$-$C_6$ alkyl, and pharmaceutically acceptable salt thereof.

2. The compound of claim 1, wherein $R^2$ is absent.

3. The compound of claim 1, wherein the combined groups Y—$R^3$—Z are $CO_2H$, OH, or CHO.

4. The compound of claim 1, wherein the compound is

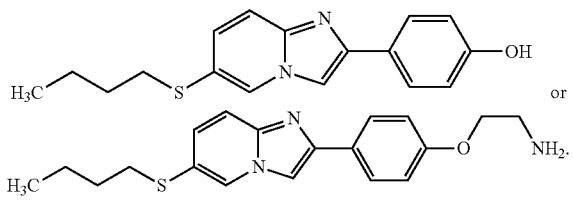

5. A method of treating cancer in a subject in need thereof by administering a therapeutically effective amount of a compound of Formula I:

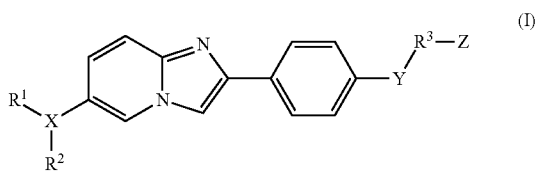

wherein X is S, Y is selected from S, CO, NH, NO, and O, $R^1$ is butyl and optional $R^2$ is selected from H, OH, substituted or unsubstituted $C_1$-$C_6$ alkyl, substituted or unsubstituted $C_4$-$C_6$ cycloalkyl or cycloheteroalkyl, and aryl;

$R^3$ is selected from H, OH, substituted or unsubstituted $C_1$-$C_6$ alkyl, and optional Z is selected from OH, $NH_2$, NH(CO)$R^4$, NH($SO_2$)$R^4$, guanidine, alkylguanidine, and fluoroguanidine, $R^4$ is polyethylene glycol or substituted or unsubstituted $C_1$-$C_6$ alkyl, and pharmaceutically acceptable salt thereof, or wherein X is selected from CH, N, S, and O, Y is selected from S, CO, NH, NO, and O, $R^1$ and optional $R^2$ are independently selected from H, OH, substituted or unsubstituted $C_1$-$C_6$ alkyl, substituted or unsubstituted $C_4$-$C_6$ cycloalkyl or cycloheteroalkyl, and aryl;

$R^3$ is substituted or unsubstituted $C_1$-$C_6$ alkyl, and Z is selected from $NH_2$, NH(CO)$R^4$, NH($SO_2$)$R^4$, guanidine, alkylguanidine, and fluoroguanidine, $R^4$ is polyethylene glycol or substituted or unsubstituted $C_1$-$C_6$ alkyl, and pharmaceutically acceptable salt thereof, and wherein the cancer is bladder cancer, prostate cancer, liver cancer, breast cancer, colon cancer, or leukemia.

6. The method of claim 5, wherein X is S, Y is selected from S, CO, NH, NO, and O, $R^1$ is butyl and optional $R^2$ is selected from H, OH, substituted or unsubstituted $C_1$-$C_6$ alkyl, substituted or unsubstituted $C_4$-$C_6$ cycloalkyl or cycloheteroalkyl, and aryl;

$R^3$ is selected from H, OH, substituted or unsubstituted $C_1$-$C_6$ alkyl, and optional Z is selected from OH, $NH_2$, NH(CO)$R^4$, NH($SO_2$)$R^4$, guanidine, alkylguanidine, and fluoroguanidine, $R^4$ polyethylene glycol or substituted or unsubstituted $C_1$-$C_6$ alkyl.

7. The method of claim 6, wherein X is selected from CH, N, S, and O, Y is selected from S, CO, NH, NO, and O, $R^1$ and optional $R^2$ are independently selected from H, OH, substituted or unsubstituted $C_1$-$C_6$ alkyl, substituted or unsubstituted $C_4$-$C_6$ cycloalkyl or cycloheteroalkyl, and aryl;

$R^3$ is substituted or unsubstituted $C_1$-$C_6$ alkyl, and Z is selected from $NH_2$, NH(CO)$R^4$, NH($SO_2$)$R^4$, guanidine, alkylguanidine, and fluoroguanidine, $R^4$ is polyethylene glycol or substituted or unsubstituted $C_1$-$C_6$ alkyl.

8. The method of claim 6, wherein $R^2$ is absent.

9. The method of claim 6, wherein the combined groups Y—$R^3$—Z are $CO_2H$, OH, or CHO.

10. The method of claim 7, wherein Y is O.

11. The method of claim 5, wherein the compound is

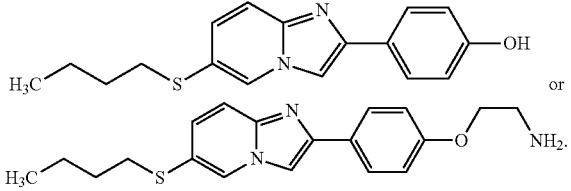

12. The method of claim 5, wherein the compound of Formula I is administered together with a pharmaceutically acceptable carrier.

13. The method of claim 5, wherein the cancer is acute myeloid leukemia.

14. The method of claim 5, wherein the subject is human.

15. A method of stimulating differentiation in a cell, comprising contacting the cell with an effective amount of a compound according to formula I:

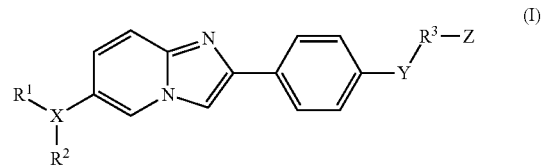

wherein X is selected from CH, N, S, and O, Y is selected from S, CO, NH, NO, and O, $R^1$ and optional $R^2$ are independently selected from H, OH, substituted or unsubstituted $C_1$-$C_6$ alkyl, substituted or unsubstituted $C_4$-$C_6$ cycloalkyl or cycloheteroalkyl, and aryl;

$R^3$ is selected from H, OH, substituted or unsubstituted $C_1$-$C_6$ alkyl, and optional Z is selected from OH, $NH_2$, $NH(CO)R^4$, $NH(SO_2)R^4$, guanidine, alkylguanidine, and fluoroguanidine, $R^4$ is polyethylene glycol or substituted or unsubstituted $C_1$-$C_6$ alkyl, and pharmaceutically acceptable salt thereof.

16. The method of claim 15, wherein the cell is a cancer cell.

17. A compound of formula I

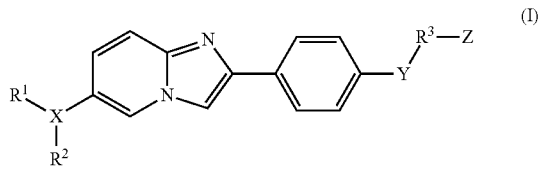

wherein X is selected from CH, N, S, and O, Y is selected from S, CO, NH, NO, and O, $R^1$ and optional $R^2$ are independently selected from H, OH, substituted or unsubstituted $C_1$-$C_6$ alkyl, substituted or unsubstituted $C_4$-$C_6$ cycloalkyl or cycloheteroalkyl, and aryl;

$R^3$ is substituted or unsubstituted $C_1$-$C_6$ alkyl, and Z is selected from $NH_2$, $NH(CO)R^4$, $NH(SO_2)R^4$, guanidine, alkylguanidine, and fluoroguanidine, $R^4$ is polyethylene glycol or substituted or unsubstituted $C_1$-$C_6$ alkyl, and pharmaceutically acceptable salt thereof.

18. The compound according to claim 17, wherein Y is O.

19. The compound according to claim 17, wherein Z is $NH_2$.

20. The compound according to claim 17, wherein Z is $NH(CO)R^4$ or $NH(SO_2)R^4$.

* * * * *